(12) United States Patent
Lim et al.

(10) Patent No.: US 10,768,111 B2
(45) Date of Patent: Sep. 8, 2020

(54) FLUORESCENT SUPRAMOLECULAR BIOSENSOR AND PREPARATION METHOD THEREOF

(71) Applicant: INDUSTRY-ACADEMIC COOPERATION FOUNDATION, YONSEI UNIVERSITY, Seoul (KR)

(72) Inventors: Yong-beom Lim, Seoul (KR); Woo-jin Jeong, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 207 days.

(21) Appl. No.: 15/988,616

(22) Filed: May 24, 2018

(65) Prior Publication Data
US 2019/0064066 A1 Feb. 28, 2019

(30) Foreign Application Priority Data

Aug. 23, 2017 (KR) ........................ 10-2017-0106595

(51) Int. Cl.
| | |
|---|---|
| G01N 21/64 | (2006.01) |
| C07K 14/00 | (2006.01) |
| C12Q 1/04 | (2006.01) |
| C07K 19/00 | (2006.01) |
| G01N 33/542 | (2006.01) |
| G01N 33/569 | (2006.01) |
| C12Q 1/6834 | (2018.01) |
| C07K 1/13 | (2006.01) |

(52) U.S. Cl.
CPC ....... *G01N 21/6428* (2013.01); *C07K 14/003* (2013.01); *C07K 19/00* (2013.01); *C12Q 1/04* (2013.01); *G01N 33/542* (2013.01); *G01N 33/56911* (2013.01); *C07K 1/13* (2013.01); *C12Q 1/6834* (2013.01); *G01N 2021/6439* (2013.01)

(58) Field of Classification Search
None
See application file for complete search history.

(56) References Cited

FOREIGN PATENT DOCUMENTS

KR    10-0760525    9/2007

OTHER PUBLICATIONS

Waltkins, A.M. et al. Protein-Protein Interactions Mediated by Helical Tertiary Structure Motifs, Journal of American Chemical Society, 137, pp. 11622-11630 (Year: 2015).*

(Continued)

*Primary Examiner* — Xiaoyun R Xu
(74) *Attorney, Agent, or Firm* — Duane Morris LLP; Gregory M. Lefkowitz

(57) ABSTRACT

The present disclosure relates to a fluorescent supramolecular biosensor, more particularly to a fluorescent supramolecular biosensor which shows change in fluorescence signal through binding to a specific bacterium and a method for preparing the same. The fluorescent supramolecular biosensor is advantageous in that it exhibits remarkably superior affinity and selectivity for a target bacterium.
In addition, because a secondary coiled coil stereostructure is highly stabilized as the supramolecular building block is self-assembled to form the fluorescent supramolecular biosensor, the fluorescent supramolecular biosensor can be stored for a long period of time without structural change even at high temperatures.

13 Claims, 18 Drawing Sheets

Specification includes a Sequence Listing.

(56) References Cited

OTHER PUBLICATIONS

Zhu, Q. et al. Combinatorial discovery of novel fluorescent dyes based on Dapoxyl, Tetrahedron Letters, 43, pp. 5083-5086 (Year: 2002).*
Merrifield, "Solid Phase Peptide Synthesis", J. Amer. Chem. Soc., vol. 85, Jul. 20, 1963, pp. 2149-2154.
Merrifield, "Solid Phase Synthesis", The Rockefeller University, Nobel Lecture, Dec. 8, 1984, pp. 149-175.
Goodsell, "Bionanotechnology, Lessons From Nature", John Wiley & Sons, Inc., 2004.
Han et al., "Macromolecular Sensing of RNAs by Exploiting Conformational Changes in Supramolecular Nanostructures", American Chemical Society, Biomacromolecules, 2014, 15, 2642-2647.
Han et al., "Bioinspired Self-Assembled Peptide Nanofibers with Thermostable Multivalent α Helices", merican Chemical Society, Biomacromolecules, 2013, 14, 1594-1599.

* cited by examiner

SEQUENCE LISTING

```
<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: the first peptide sequence on alpha-helical
      coiled-coil self-assembling unit

<400> SEQUENCE: 1

Arg Leu Arg Lys Leu Arg Lys Lys Leu Arg Ser Gly Ala
1               5                   10

<210> SEQ ID NO 2
<211> LENGTH: 21
<212> TYPE: PRT
<213> ORGANISM: Artificial Sequence
<220> FEATURE:
<223> OTHER INFORMATION: the first peptide sequence on alpha-helical
      coiled-coil self-assembling unit

<400> SEQUENCE: 2

Lys Glu Leu Glu Asp Lys Gln Glu Arg Leu Arg Lys Leu Arg Lys Lys
1               5                   10                  15

Leu Arg Ser Gly Ala
            20

<210> SEQ ID NO 3
<211> LENGTH: 13
<212> TYPE: PRT
<213> ORGANISM: Artificial Sequence
<220> FEATURE:
<223> OTHER INFORMATION: bacteria-binding peptide

<400> SEQUENCE: 3

Arg Leu Leu Phe Arg Lys Ile Arg Arg Leu Lys Arg Lys
1               5                   10
```

```
<210> SEQ ID NO 4
<211> LENGTH: 14
<212> TYPE: PRT
<213> ORGANISM: Artificial Sequence
<220> FEATURE:
<223> OTHER INFORMATION: bacteria-binding peptide

<400> SEQUENCE: 4

Phe Lys Arg Ile Val Gln Arg Ile Lys Asp Phe Leu Arg Lys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: the third peptide sequence on alpha-helical
      coiled-coil self-assembling unit

<400> SEQUENCE: 5

Gly Asn Ala Asp Glu Leu Tyr Lys Glu Leu Glu Asp Lys Gln
1               5                   10

<210> SEQ ID NO 6
<211> LENGTH: 7
<212> TYPE: PRT
<213> ORGANISM: Artificial Sequence
<220> FEATURE:
<223> OTHER INFORMATION: the third peptide sequence on alpha-helical
      coiled-coil self-assembling unit

<400> SEQUENCE: 6

Gly Asn Ala Asp Glu Leu Tyr
1               5
```

FLUORESCENT SUPRAMOLECULAR BIOSENSOR AND PREPARATION METHOD THEREOF

CROSS-REFERENCE TO RELATED APPLICATIONS

This application claims, under 35 U.S.C. § 119, the priority of Korean Patent Application No. 10-2017-0106595 filed on Aug. 23, 2017 in the Korean Intellectual Property Office, the disclosure of which is incorporated herein by reference in its entirety.

TECHNICAL FIELD

The present disclosure relates to a fluorescent supramolecular biosensor, more particularly to a fluorescent supramolecular biosensor which shows change in fluorescence signal through binding to a specific bacterium and a method for preparing the same.

BACKGROUND

In our daily lives, we are unconsciously exposed to surfaces contaminated by microorganisms that may cause diseases. In Korea, these microbial contaminations cause deaths of children and elderly people and lots of people catch diseases caused by various microbes.

Microbial contamination of food is also a global problem. *Salmonella*, *E. coli* and other food-derived microbes cause innumerable diseases every year. Acute symptoms include nausea, vomiting, abnormal stomachache, diarrhea, fever and headache. Chronic results may follow the onset of the acute symptoms. Because microbes derived from meat, fish and poultry can be delivered to uncooked food through cross contamination, it will be of great help if the presence of microbes on the kitchen countertop can be detected simply. In addition, in order to ensure the stability of food in food processing industry or to prevent deterioration when producing fermentation products such as beer, it is necessary to quickly detect the presence of microbes.

In general, as methods for detecting pathogenic microorganisms, monitoring of symptoms, observation using a microscope, immunological detection of specific antigens of pathogenic microorganisms, amplification of specific genes through the PCR technology, etc. are used. Although the PCR method allows for very precise and accurate detection, it is greatly affected by several factors because the process of gene amplification is necessary. For the microscopic method to be applicable, the pathogenic organisms should be large enough to be observable with a microscope and should have high density to be easily detectable from a sample. In addition, their morphology should be clearly distinguishable from other organisms.

Therefore, development of a diagnostic sensor capable of detecting microorganisms more accurately and quickly is necessary.

REFERENCES OF THE RELATED ART

Patent Document

Patent document 1. Korean Patent Registration No. 10-0760525.

Non-Patent Document

Non-patent document 1. Goodsell, D. S. Bionanotechnology: Lessons from Nature; Wiley-Liss: Hoboken, 2004.

SUMMARY

The present disclosure is directed to providing a fluorescent supramolecular biosensor.

The present disclosure is also directed to providing a method for preparing the fluorescent supramolecular biosensor on a large scale.

The present disclosure provides a supramolecular biosensor for detecting a bacterium, containing a plurality of supramolecular building blocks composed of: (1) a first peptide having a coiled coil structure; (2) an α-helical second peptide binding specifically to *E. coli*; and (3) a third peptide having a fluorophore bound.

The supramolecular building block may be a lariat-type polypeptide wherein the first and second peptides are bound centered around a lysine residue to form a linear peptide, the linear peptide forms a cyclic structure as both ends of are bound through a cyclization process and the third peptide is bound to a nitrogen atom of a main chain amine group (α-amine group) of the lysine residue of the linear peptide.

The fluorescent supramolecular biosensor may be a tetramer formed from the four supramolecular building blocks.

The supramolecular building block may further contain a linker connecting the first and second peptides.

The first peptide may be represented by SEQ ID NO 1 or 2.

The second peptide may be represented by SEQ ID NO 3 or 4.

The third peptide may be represented by SEQ ID NO 5 or 6.

The supramolecular building block may form a tetramer through self-assembly when pH is 6.0-7.0 or ionic strength is 0.01-0.3 M.

The fluorescent supramolecular biosensor may show change in the fluorescence signal of the fluorophore as a folded structure formed in the supramolecular building block is changed through binding to a target bacterium.

The fluorescent supramolecular biosensor may be a spherical nanoparticle with an average particle diameter of 5-20 nm.

The supramolecular building block may be represented by Chemical Formula 1, as shown in FIG. 10.

In the chemical formula shown in FIG. 10, $R_1$ is DEABA (p-(N,N-diethylamino)benzoic acid) or Dapoxyl.

The fluorescent supramolecular biosensor may maintain a molar ellipticity ($[\theta]_{222}/[\theta]_{208}$) of 1-0.8 at 20-90° C.

The fluorophore may be one selected from a group consisting DEABA (p-(N,N-diethylamino)benzoic acid), SNAFL, SNARF, SNAFL, Calcium Green, Amplex Red, Texas Red, BIODIPY, Oregon Green, Alexa Fluor, Cascade Blue, Dapoxyl, coumarin, rhodamine, N-methyl-4-hydrazino-7-nitrobenzofurazan, dansylethylenediamine, dansylcadaverine and dansylhydrazine.

The present disclosure also provides a method for detecting a bacterium using the fluorescent supramolecular biosensor.

The detection method may include a step of irradiating light for fluorescence excitation and a step of detecting fluorescence emission.

The fluorescent supramolecular biosensor according to the present disclosure shows change in fluorescence emission as structural change of the supramolecular building blocks is induced due to multiple bonding with a specific bacterium. Accordingly, the fluorescent supramolecular biosensor and the detection method using the same are advantageous in that selectivity for the specific bacterium is high and the change in its concentration can be detected more accurately.

The fluorescent supramolecular biosensor according to the present disclosure, which is formed from the binding of the plurality of supramolecular building blocks having new structural characteristics, is advantageous in that affinity and selectivity for the target bacterium are remarkably superior.

In addition, the fluorescent supramolecular biosensor can be stored at high temperatures for a long period of time with little structural change because the 3-dimensional coiled coil structure is very firmly stabilized as the supramolecular building blocks are self-assembled to form the fluorescent supramolecular biosensor.

Figure 4A:
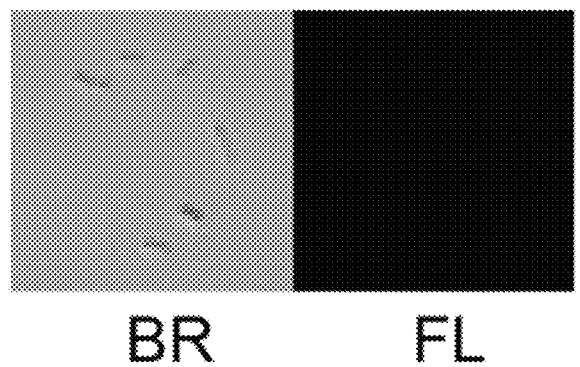
FIG. 4A shows an optical microscopic image (BR: bright field) and a fluorescence image (FL) obtained by confocal laser scanning microscopy (CLSM) of a solution in which only a bacterium exists.

As seen from FIG. 4A, no fluorescence was emitted when only the bacterium existed. But, fluorescence was observed when the fluorescent supramolecular biosensor according to the present disclosure was added.

Figure 5A:
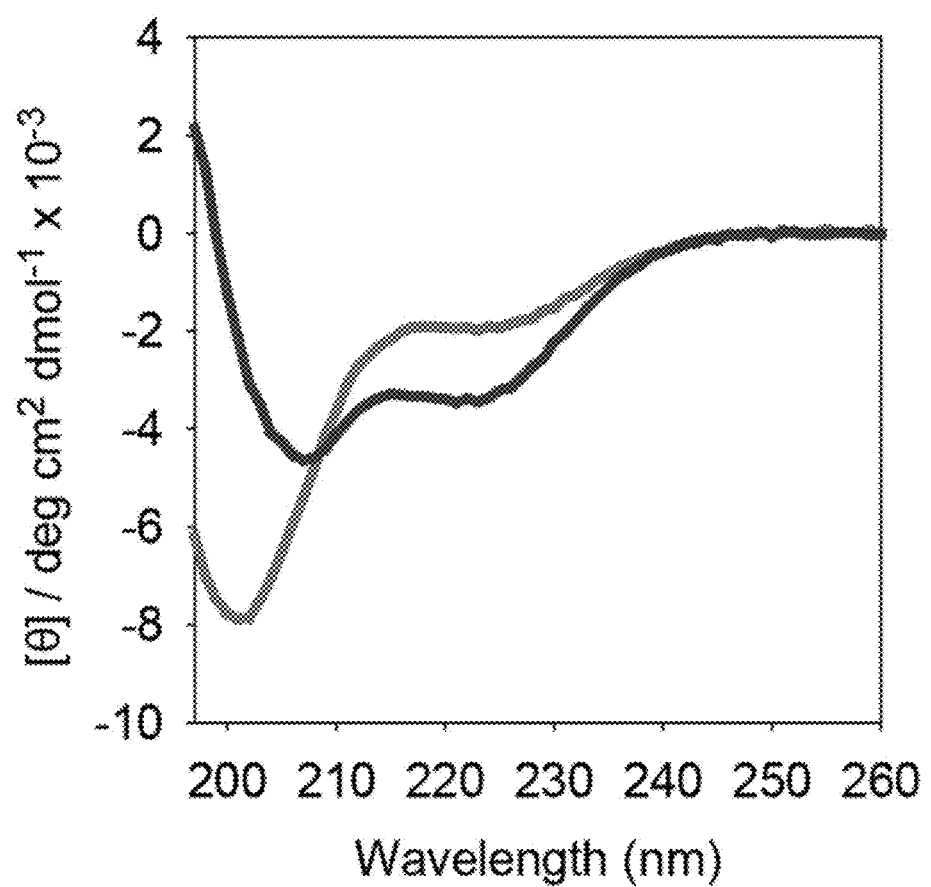
Figure 5B:
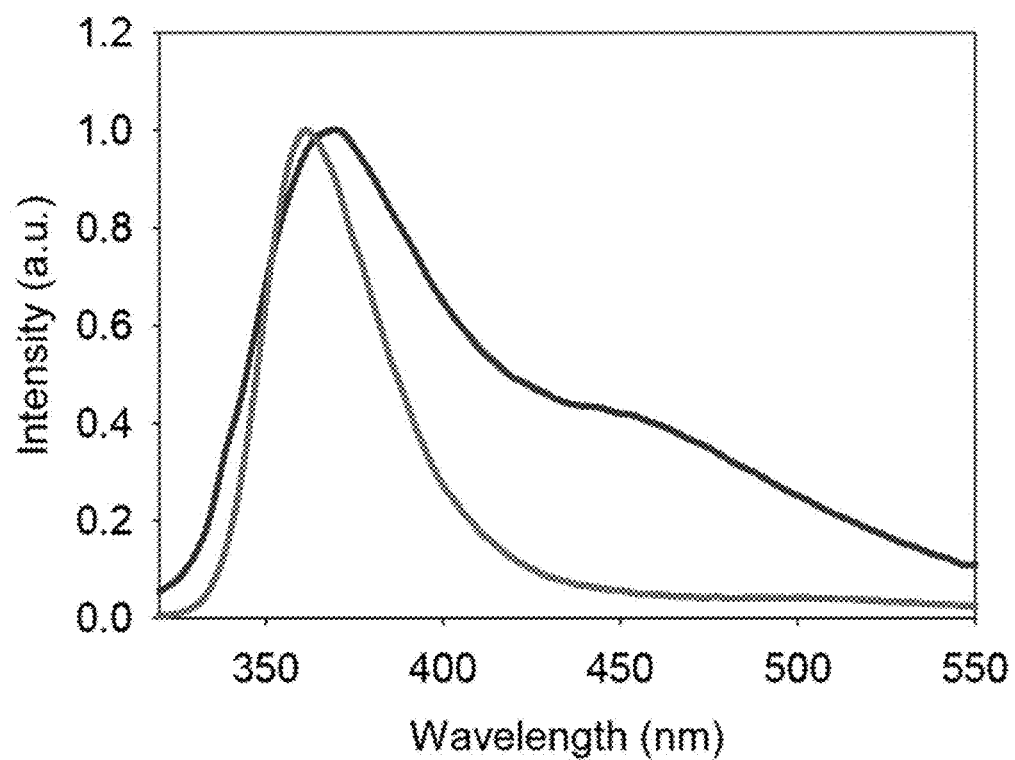
Figure 5C:
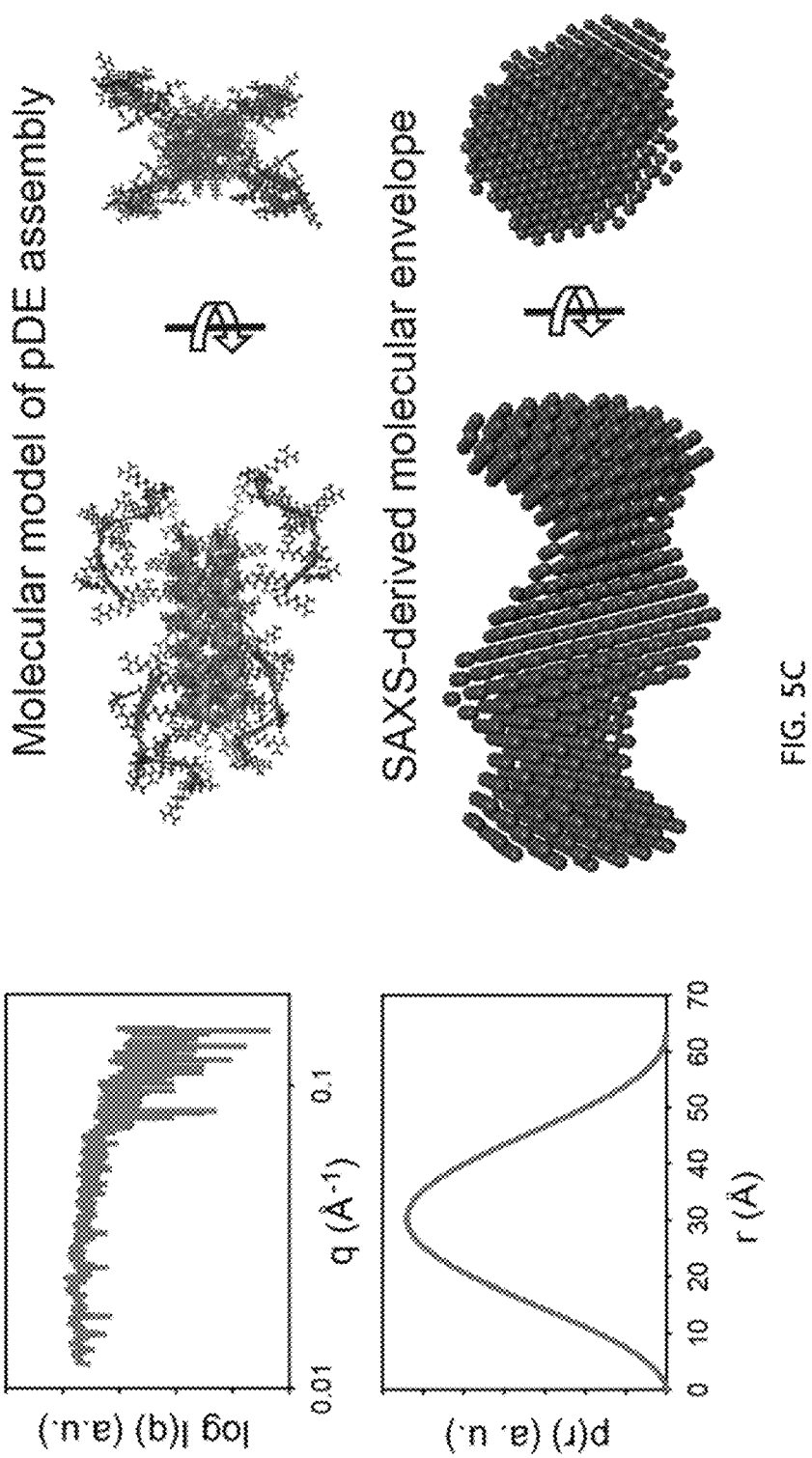

FIGS. 5A to 5C show results of investigating whether a supramolecular building block (pDE) prepared in Preparation Example 1 forms a tetramer and operates as a fluorescent supramolecular biosensor when dissolved in a solvent. FIG. 5A shows CD spectra obtained when the pDE of Preparation Example 1 was dissolved in pure water (red) and PBS (20 mM potassium phosphate, 150 mM NaCl, pH 7.0; blue), respectively, and FIG. 5B shows fluorescence intensity depending on wavelength.

FIG. 5C shows an SAXS result for the stereostructure of a fluorescent supramolecular biosensor formed as a tetramer from pDE prepared in Preparation Example 1.

Figure 6A:
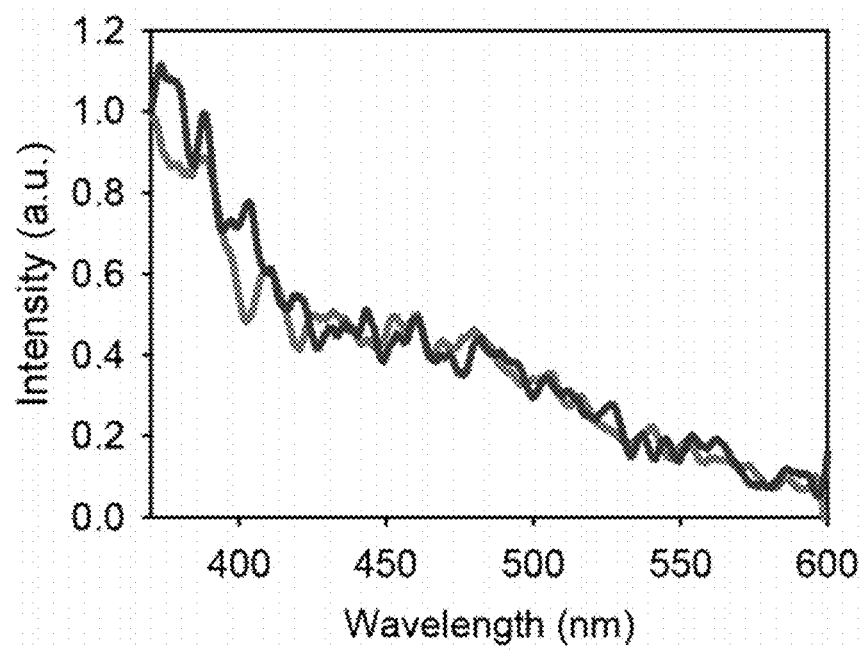
Figure 6B:
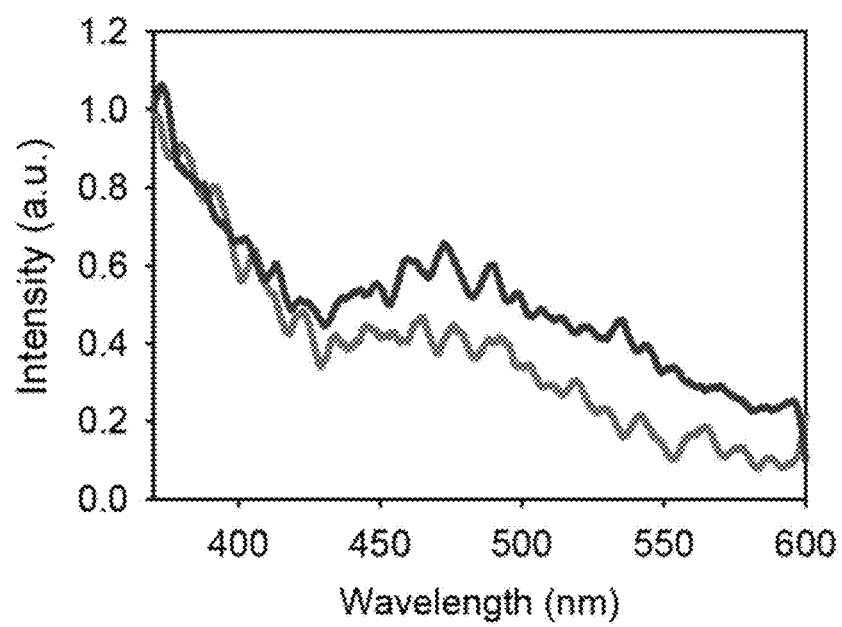
Figure 6C:
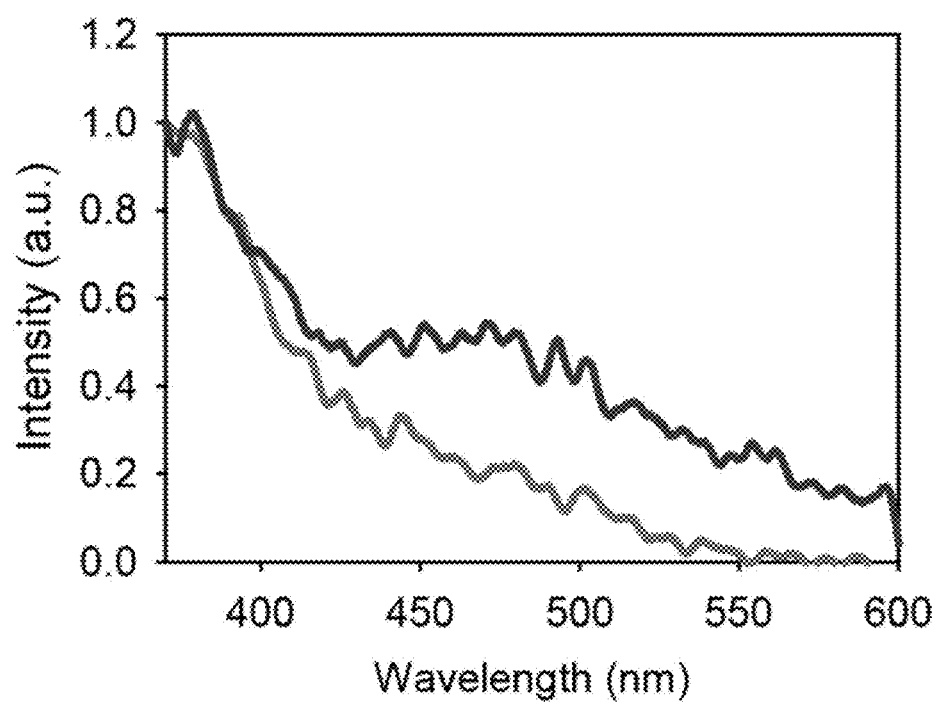

FIGS. 6A to 6C show results of investigating the change in fluorescence after adding pDE of Preparation Example 1 to mixture solutions of E. coli and Staphylococcus aureus (S. aureus) at various concentrations: in FIG. 6A, $10^5$ CFU/mL, in FIG. 6B, $10^6$ CFU/mL, and in FIG. 6C, $10^5$ CFU/mL. All experiments were conducted at room temperature. In the graphs, the red lines are the fluorescence signals of Preparation Example 1 pDE mixed with E. coli and the blue lines are the fluorescence signals of Preparation Example 1 pDE mixed with Staphylococcus aureus.

Figure 7A:
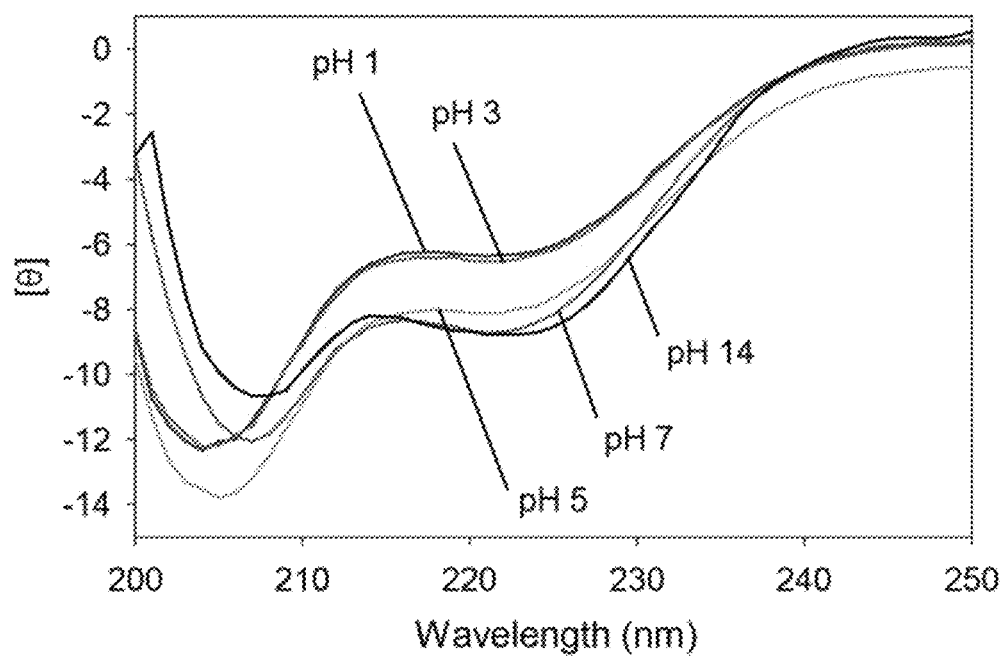
Figure 7B:
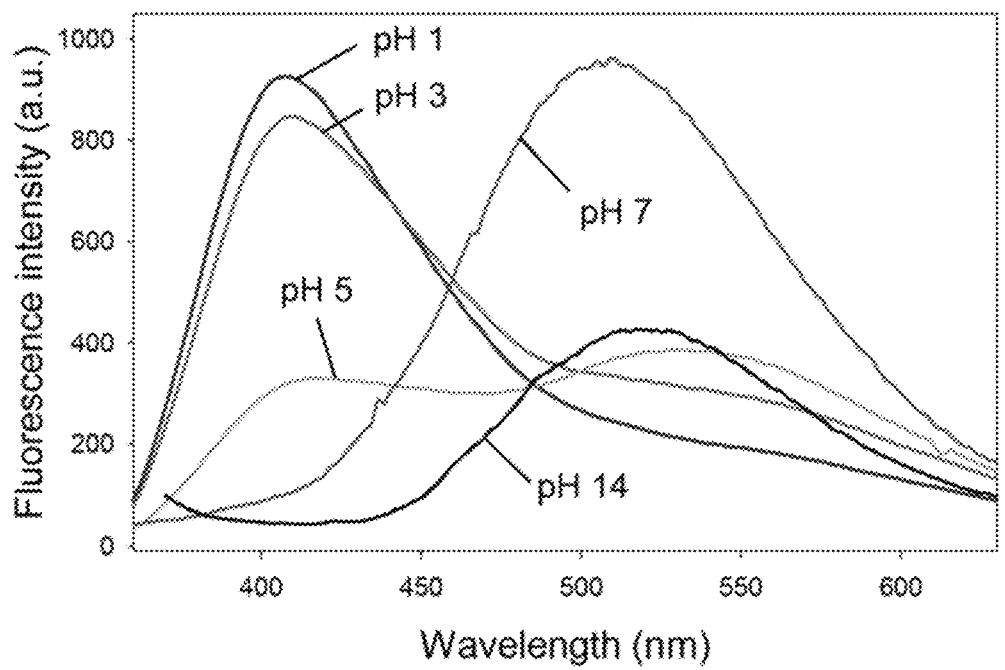

FIGS. 7A to 7F show results of investigating the E. coli sensing and self-assembly of a fluorescent supramolecular biosensor prepared from pDA (Preparation Example 2). FIG. 7A shows the CD spectra of a fluorescent supramolecular biosensor prepared from pDA (Preparation Example 2) under various pH conditions and FIG. 7B shows the CD spectra of pDA of Preparation Example 2 under various pH conditions. The pH was controlled with HCl or NaOH in the presence of 150 mM NaCl. [pDA]=20 µM.

Figure 7C:
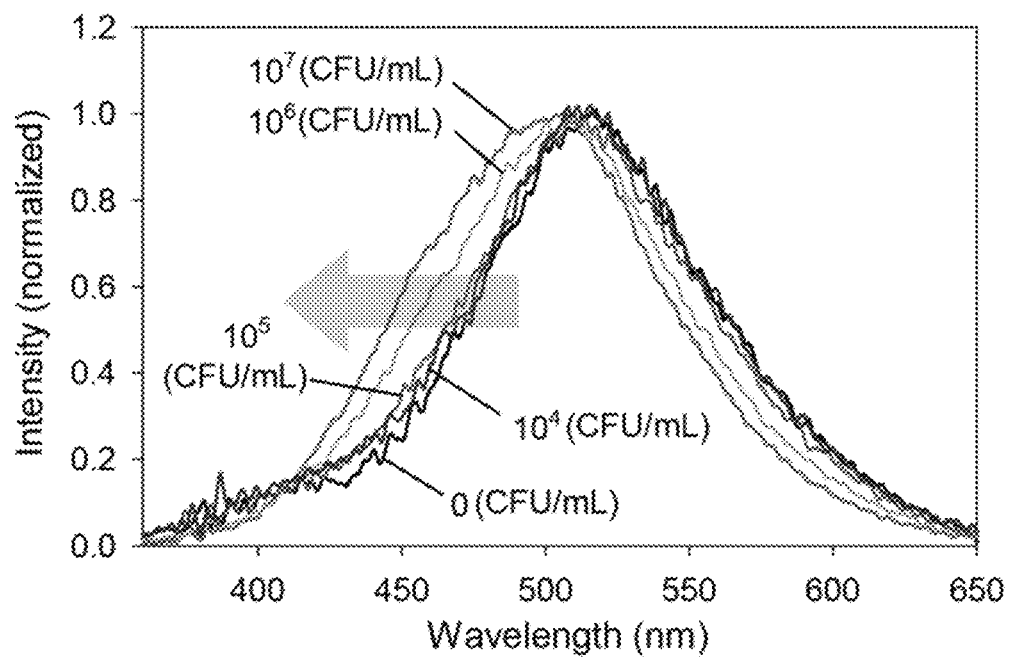
Figure 7D:
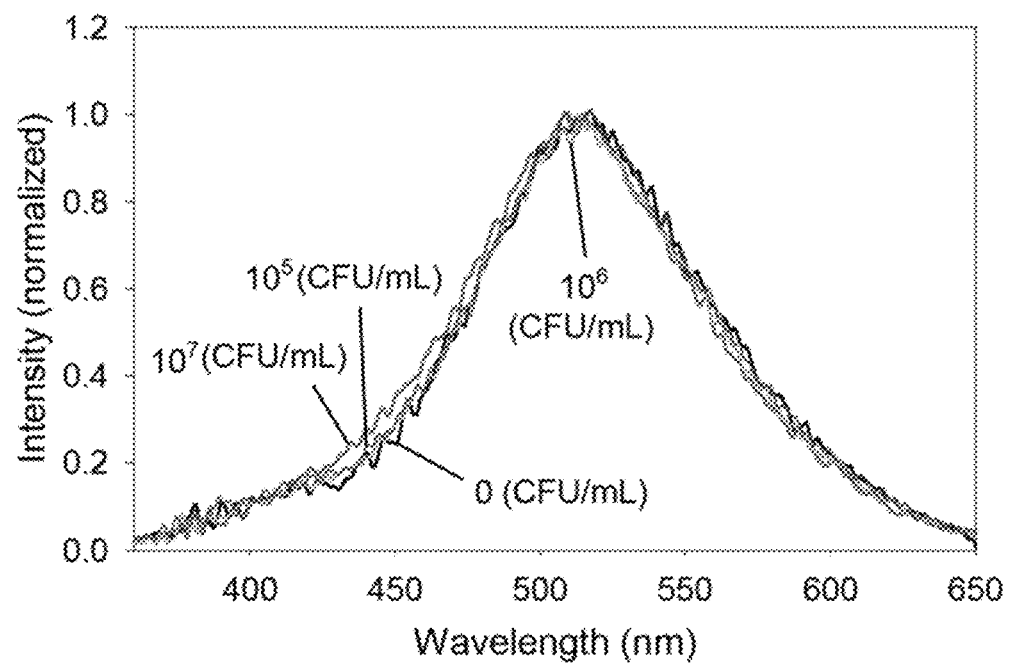

FIG. 7C shows the normalized fluorescence emission spectra obtained by mixing E. coli of various concentrations with the fluorescent supramolecular biosensor prepared from the pDA of Preparation Example 2 and measuring fluorescence intensity and FIG. 7D shows the normalized fluorescence emission spectra obtained by mixing Staphylococcus aureus (S. aureus) of various concentrations with the fluorescent supramolecular biosensor prepared from the pDA of Preparation Example 2 and measuring fluorescence intensity.

Figure 7E:
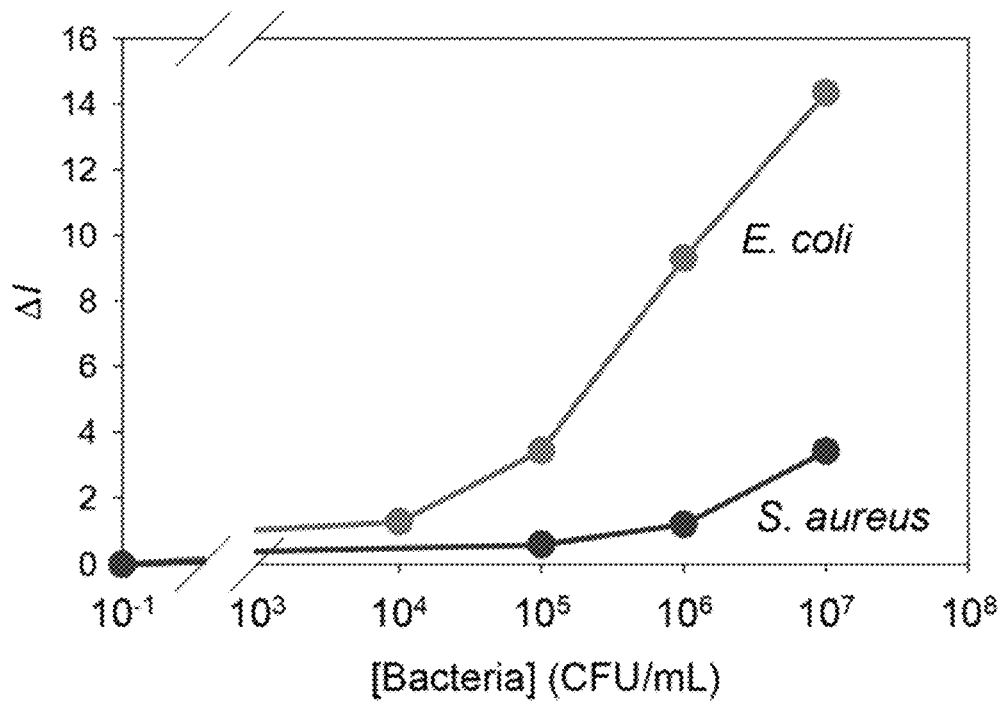

FIG. 7E shows a graph obtained by measuring the change in fluorescence intensity (ΔI) depending on the bacterial concentration from the results of FIG. 7C and d). ΔI=fluorescence intensity of the mixture—fluorescence intensity when only the fluorescent supramolecular biosensor exists only.

Figure 7F:
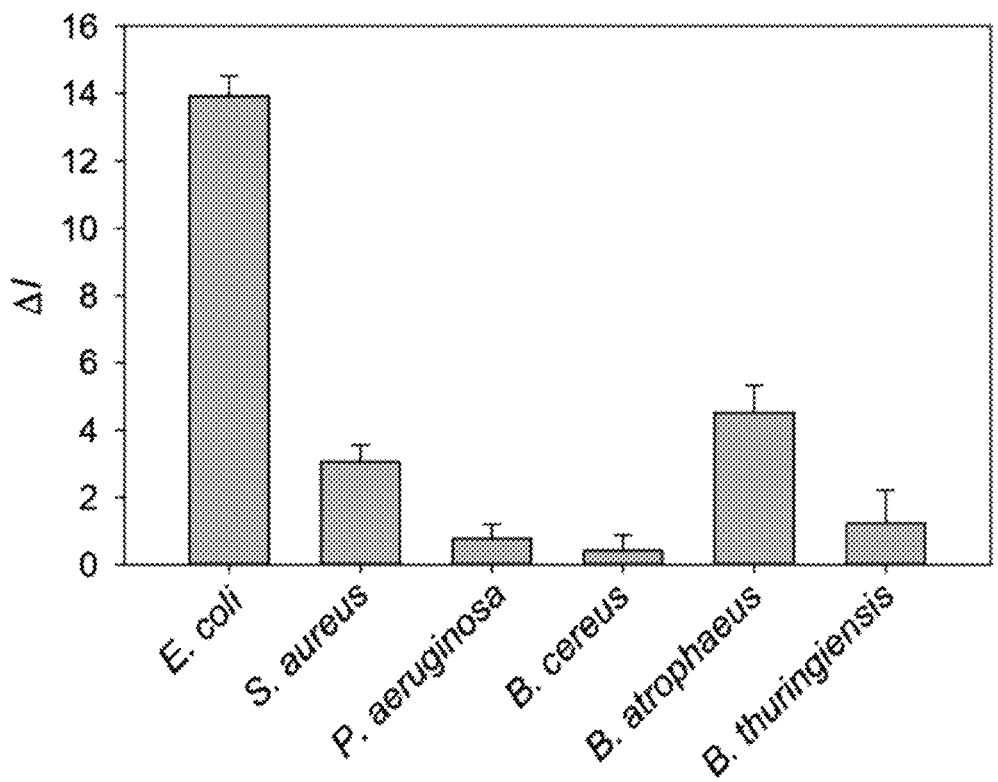

FIG. 7F shows the selectivity of the fluorescent supramolecular biosensor according to the present disclosure when the concentration of each bacterium was $10^7$ CFU/mL. All the experiments in FIGS. 7A and 7F were conducted at room temperature.

Figure 8A:
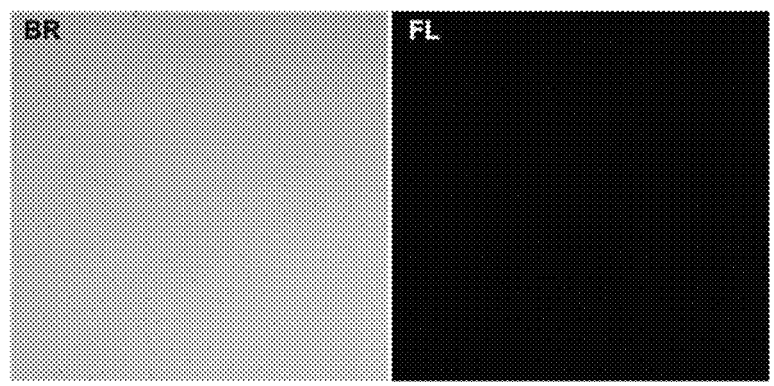
Figure 8B:
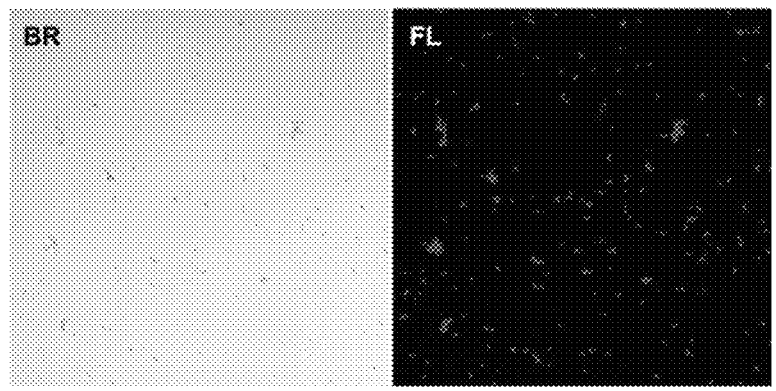

FIG. 8A shows an optical microscopic image (BR: bright field) and a fluorescence image (FL) obtained by confocal laser scanning microscopy (CLSM) of a solution in which only E. coli exists and FIG. 8B shows an optical microscopic image (BR: bright field) and a fluorescence image (FL) obtained by confocal laser scanning microscopy (CLSM) of a mixture of a fluorescent supramolecular biosensor formed from pDA of Preparation Example 2 and a bacterium (E. coli).

Figure 9A:
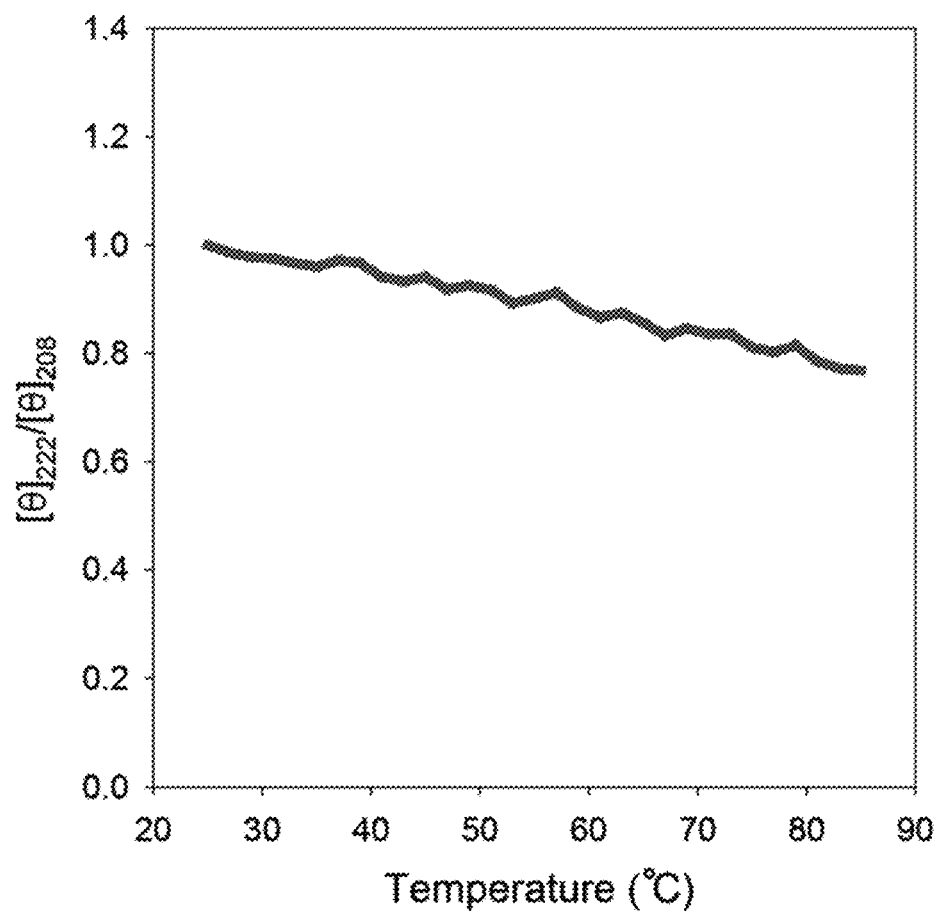
Figure 9B:
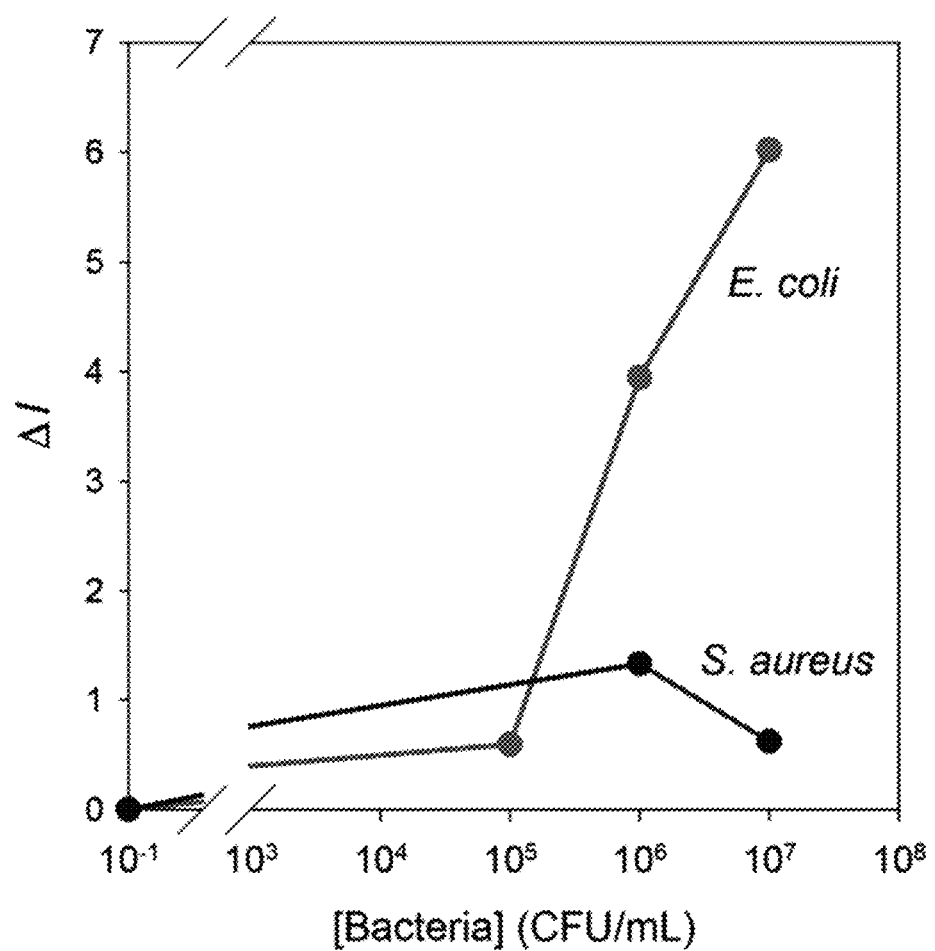

FIGS. 9A and 9B show results of investigating the thermal stability of a fluorescent supramolecular biosensor according to the present disclosure. FIG. 9A shows the CD spectrum ($[\theta]_{222}/[\theta]_{208}$) of a fluorescent supramolecular biosensor formed from pDA of Preparation Example 2 depending on temperature change. FIG. 9B shows a result of calculating the change in fluorescence intensity (ΔI) at 50° C. depending on the bacterial concentration. ΔI=fluorescence intensity of the mixture—fluorescence intensity when only the fluorescent supramolecular biosensor exists only.

Figure 10:
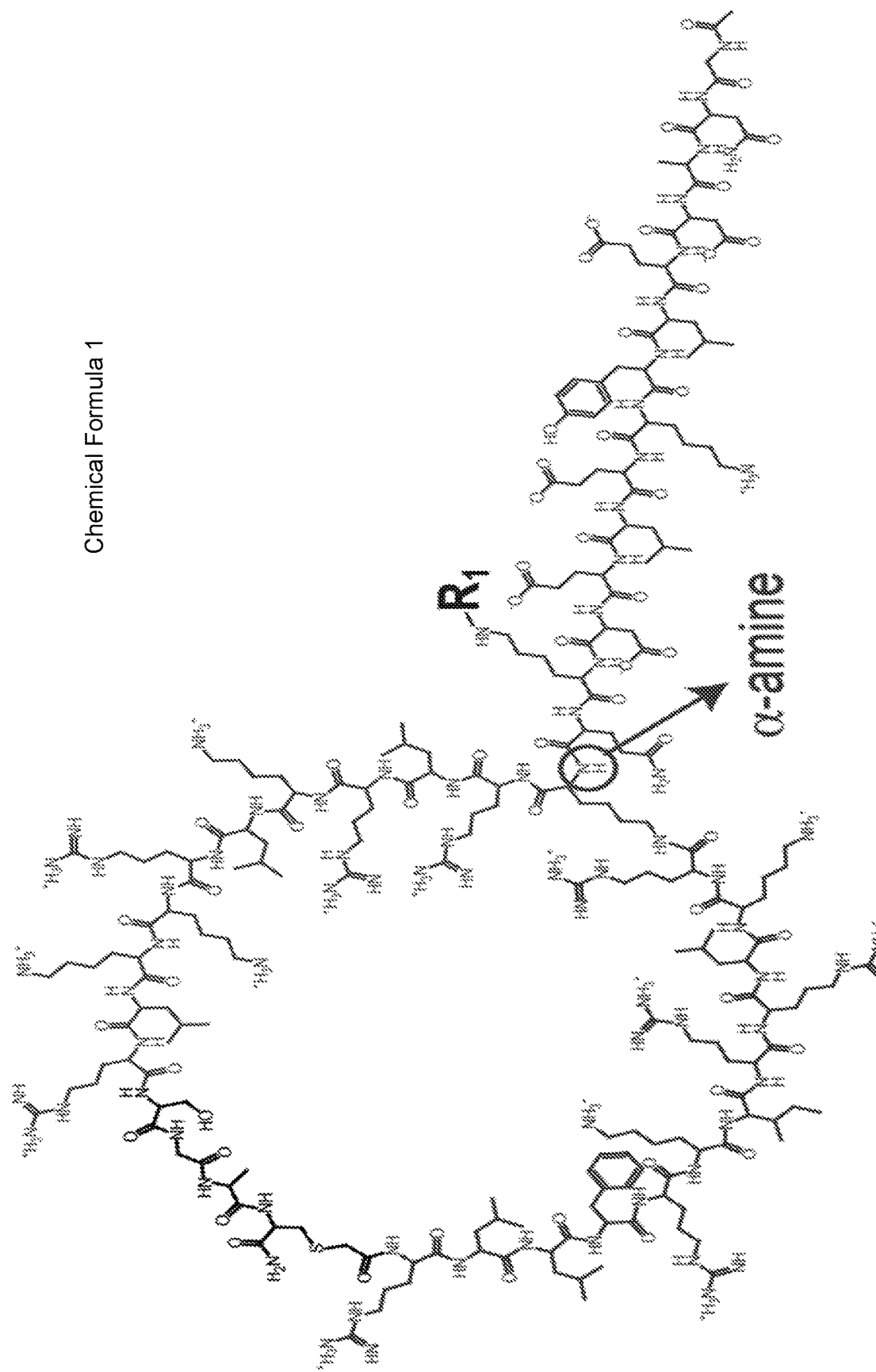

FIG. 10 shows a supramolecular building block in which $R_1$ is DEABA (p-(N,N-diethylamino)benzoic acid) or Dapoxyl.

Figure 11:
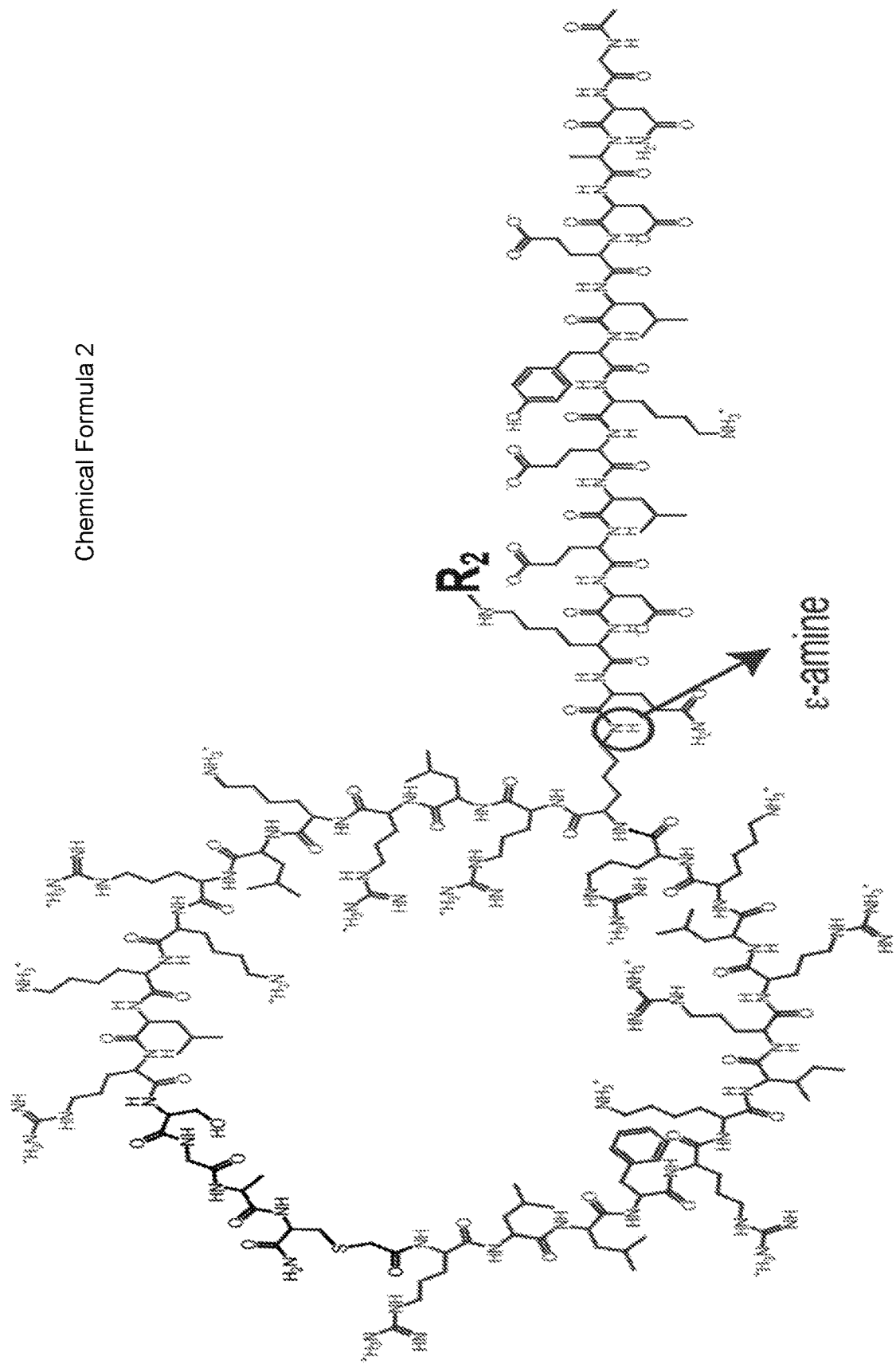

FIG. 11 shows a second supramolecular building block in which $R_2$ is DEABA (p-(N,N-diethylamino)benzoic acid) or Dapoxyl.

DETAILED DESCRIPTION OF EMBODIMENTS

Hereinafter, various aspects and exemplary embodiments of the present disclosure are described in more detail.

A fluorescent chemosensor serving as a sensor basically consists of a receptor, a signal transducer and a detector. When the chemosensor is contacted with a material to be analyzed, the molecular state of the sensor is changed through interaction and a fluorescence signal is generated.

A similar principle is applied to a fluorescent biosensor as the chemosensor. However, the receptor should be capable of interacting with broad biopolymers unlike the receptor of the chemosensor. According to a theory proposed by H. R. Crane, if it is desired to improve binding specificity when two molecules or materials interact, it is necessary to form multiple weak bonds completely. This is because self-assembly is achieved only when the surface configuration of the interacting molecules or materials is perfectly matched and the multiple weak bonds interact at proper locations.

For protein-protein interactions (PPIs), it is difficult to form multiple weak bonds or interactions at proper locations with a compound having a small molecular weight because the corresponding contact area (interface) is broad and shallow. In contrast, because peptides have conformational and binding specificity enough to form specific interactions with bulky biopolymer interfaces, PPIs based thereon are being developed.

The inventors of the present disclosure have made efforts to develop a new biosensor capable of targeting a specific bacterium with superior accuracy by using a peptide rather than a protein. They have extensively investigated elaborately designed self-assembled peptide nanostructures (hereinafter, referred to as SPNs) formed from binding of a plurality of peptides.

As a result, they have identified that the self-assembled peptide nanostructures have superior morphological characteristics and molecular recognition abilities and can be prepared simply through self-assembly based on the delicate balancing of attracting and repelling forces. In addition, they have identified that the morphology, size and function of the nanostructures are controlled by precisely controlling the directional force of self-assembly when forming the nanostructures and have completed the present disclosure.

In the present disclosure, the term "peptide" refers to a linear molecule formed as amino acid residues are bound to each other through peptide bonding.

Representative amino acids and their acronyms are alanine (Ala, A), isoleucine (Ile, I), leucine (Leu, L), methionine (Met, M), phenylalanine (Phe, F), proline (Pro, P), tryptophan (Trp, W), valine (Val, V), asparagine (Asn, N), cysteine (Cys, C), glutamine (Gin, Q), glycine (Gly, G), serine (Ser, S), threonine (Thr, T), tyrosine (Tyr, Y), aspartic acid (Asp, D), glutamic acid (Glu, E), arginine (Arg, R), histidine (His, H) and lysine (Lys, K).

The peptide of the present disclosure may be prepared by a chemical synthesis method known in the art, particularly by the solid-phase synthesis technique (Merrifield, *J. Amer. Chem. Soc.* 85: 2149-54 (1963); Stewart, et al., Solid Phase Peptide Synthesis, 2nd. ed., Pierce Chem. Co.: Rockford, 111 (1984)).

In the present disclosure, the term "self-assembly" refers to assembly induced by noncovalent bonding (hydrogen bonding, ionic bonding, van der Waals bonding, hydrophobic bonding, electrostatic bonding, etc.).

An aspect of the present disclosure relates to a fluorescent supramolecular biosensor for detecting a bacterium, containing a plurality of supramolecular building blocks composed of:

(1) a first peptide having a coiled coil structure;
(2) an α-helical second peptide binding specifically to a specific bacterium; and
(3) a third peptide having a fluorophore bound.

The fluorescent supramolecular biosensor is a self-assembled peptide nanostructure (SPN) with a specific secondary structure, formed as a plurality of supramolecular building blocks are self-assembled. The specific secondary structure is an α-helical coiled coil structure.

The first peptide (1) having a coiled coil structure provides structural stability and a basis for formation of a tetramer, the α-helical second peptide (2) binding specifically to a specific bacterium is a bioreceptor which serves as a peptide recognizing multiple bacteria (oligovalent peptide) and the (3) third peptide fluorophore having a fluorophore bound serves as a transducer.

Accordingly, the fluorescent supramolecular biosensor formed as the supramolecular building blocks are self-assembled satisfies all the requirements of a sensor although it has a simple structure and a very small size.

The supramolecular building block is a lariat-type polypeptide wherein the first and second peptides are bound centered around a lysine residue to form a linear peptide, the linear peptide forms a cyclic structure as both ends of are bound through a cyclization process and the third peptide is bound to a nitrogen atom of a main chain amine group (α-amine group) of the lysine residue of the linear peptide.

Figure 1:
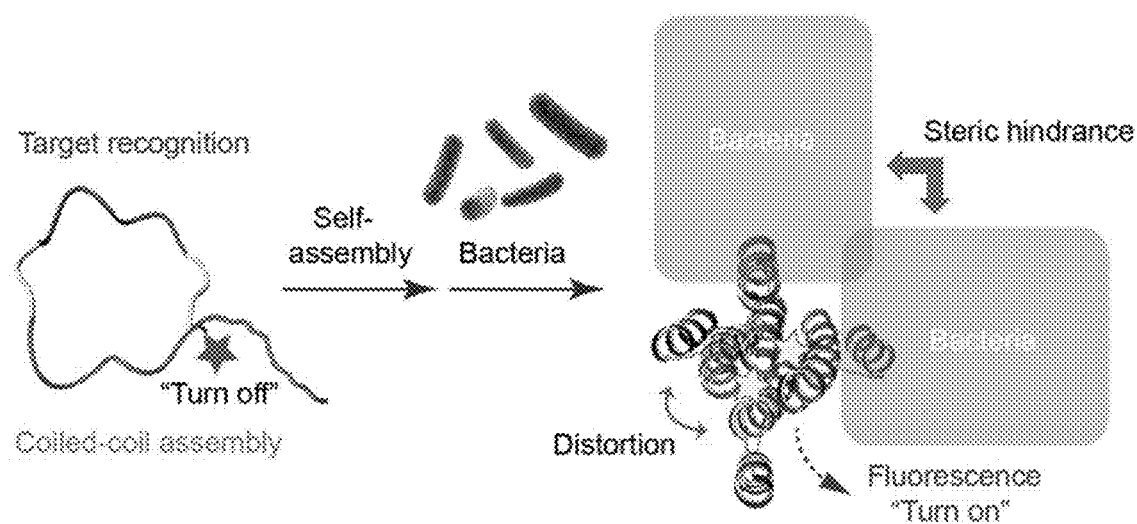
FIG. 1 shows the structure and operating principle of a supramolecular building block and a fluorescent supramolecular biosensor containing the same according to the present disclosure.

In the present disclosure, the lariat-type refers to a shape of one ring from which a tail extends, as shown in FIG. 1. The supramolecular building block according to the present disclosure is composed of a peptide portion (first peptide and second peptide) forming one cyclic (ring) structure and one peptide (third peptide) of a tail shape extending from the cyclic structure.

The supramolecular building block is a structural element for preparing the fluorescent supramolecular biosensor. In the supramolecular building block, the second peptide having an α-helical secondary structure determines the selectivity for a target bacterium and the selectivity, sensitivity and thermal stability of the fluorescent supramolecular biosensor for the target bacterium may be determined by how and where the second peptide is bound to the first peptide.

The fluorescent supramolecular biosensor is composed of the four supramolecular building blocks. When the second peptide of the supramolecular building block serving as a bioreceptor is bound to the target bacterium, structural change is induced for the interaction between the supramolecular building blocks and change in a fluorescence signal is observed from the third peptide.

When the first peptide forms a cyclic peptide through cyclization with the second peptide, the second peptide also has a coiled coil structure such as an α-helical structure as the first peptide. The coiled coil structure of the cyclic peptide is stably fixed and constrained by the cyclization, thereby exhibiting superior stability.

Figure 4B:
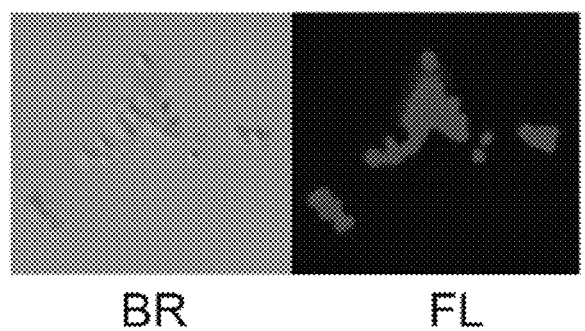
FIG. 4B shows an optical microscopic image (BR: bright field) and a fluorescence image (FL) obtained by confocal laser scanning microscopy (CLSM) of a mixture of a fluorescent supramolecular biosensor according to the present disclosure (Preparation Example 1 pDE) and a bacterium (E. coli).

The α-helical structure of the second peptide formed by the first peptide plays a very important role in recognizing a Gram-negative bacterium (*E. coli*), which can be confirmed from FIGS. 4A and 4B.

The cyclic structure of the first peptide and the second peptide may be formed through the following bonding.

i) The N-terminal of the second peptide may be connected to the C-terminal of the first peptide via a linker (first bonding) and ii) a lysine residue existing at the N-terminal of the first peptide may be bound to the C-terminal of the second peptide (second bonding). The second peptide may be bound to a side chain amine group (ε-amino group) of the lysine residue of the first peptide.

Specifically, when the second peptide is bound to the side chain amine group (ε-amino group) of the lysine residue existing at the N-terminal of the first peptide, the α-helical structure of the first peptide is fixed very stably, so that the stable secondary structure (coiled coil structure) can be maintained for a long time even in a buffer or an aqueous solution.

That is to say, the supramolecular building block (hereinafter, also referred to as fBS) of the present disclosure is advantageous in that it is capable of detecting the target bacterium selectively and maintains its function or structure at high temperatures due to superior heat resistance. The fBS is advantageous in that it provides a new stable and biologically safe supramolecular building block that can be used under extreme and harsh environments.

As described above, the supramolecular building block is a lariat-type polypeptide having a stabilized α-helical coiled coil structure, which is formed through self-assembly due to interaction between the polypeptide chains and whose structure changes reversibly depending on environments. Specifically, the supramolecular building block has an α-helical coiled coil structure, which is formed through self-assembly due to interaction between the chains of the first, second and peptides and exhibits reversible change. In the lariat-type polypeptide supramolecular building block, the first peptide and the third peptide contain both cyclic and linear self-assembling units whereas the second peptide capable of targeting the bacterium contains only the cyclic unit.

The first peptide is a part of a cyclic peptide which forms a cyclic structure through grafting with the second peptide. Specifically, it contains an amino acid sequence located on a turn selected from the 4-6th turns with respect to the 1st turn of the cyclic peptide.

The amino acid sequence located on one selected from the 4-6th turns is a lysine residue. Specifically, if it is not a lysine residue, it may be replaced with a lysine residue.

The first peptide may have a SEQ ID NO 1 or 2 (N'→C').

[SEQ ID NO 1]
Arg Leu Arg Lys Leu Arg Lys Lys Leu Arg Ser Gly

Ala

[SEQ ID NO 2]
Lys Glu Leu Glu Asp Lys Gln Glu Arg Leu Arg Lys

Leu Arg Lys Lys Leu Arg Ser Gly Ala

And, in the supramolecular building block, the second peptide is a peptide capable of specifically recognizing the target bacterium and forming interaction. It is not particularly limited as long as it contains an amino acid sequence capable of specifically binding to the specific bacterium and having a coiled coil structure (α-helix). Specifically, the amino acid sequence may be selected from SEQ ID NOS 3 or 4.

[SEQ ID NO 3]
Arg Leu Leu Phe Arg Lys Ile Arg Arg Leu Lys Arg

Lys

[SEQ ID NO 4]
Phe Lys Arg Ile Val Gln Arg Ile Lys Asp Phe Leu

Arg Lys

The first peptide and the second peptide may be connected directly or via a linker. The linker improves the flexibility and stability of the first peptide and the second peptide. The linker may be one or more selected from compounds represented by Chemical Formula 3 and Chemical Formula 4, an amino acid sequence wherein 1-5 glycine(s) is(are) bound continuously, one or more amino acid sequence selected from a group consisting of glycine-serine, glycine-serine-glycine-serine, glycine-glycine-serine and glycine-glycine-glycine-serine and a combination of one of the above compounds and one of the above amino acid sequences.

[Chemical Formula 3]

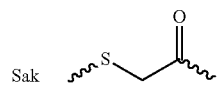

[Chemical Formula 4]

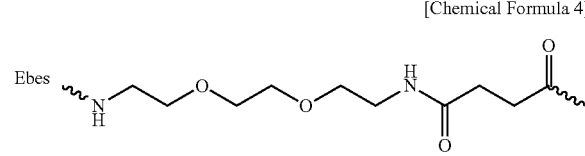

The third peptide not forming the cyclic peptide serves as a tail extended from the cyclic structure of the lariat. The first and third peptides are synthesized first as linear peptides and they are divided into the first and third peptides as the second peptide is grafted. Specifically, the third peptide may contain an amino acid sequence which forms a 5-7th, 6-7th or 7th turn based on the 1st turn of the cyclic peptide.

The third peptide may contain SEQ ID NO 5 or 6.

[SEQ ID NO 5]
Gly Asn Ala Asp Glu Leu Tyr Lys Glu Leu Glu Asp

Lys Gln

[SEQ ID NO 6]
Gly Asn Ala Asp Glu Leu Tyr

The first peptide which forms the cyclic structure by binding with the second peptide stably maintains the α-helical structure. Through this, it allows the fluorescent supramolecular biosensor to be formed through hydrophobic interaction between the supramolecular building blocks.

Although the third peptide contains the α-helical amino acid sequence, it exists as an unfolded linear form because it protrudes out of the lariat-type building block rather than being located in the cyclic structure. It ensures the structural stability of the fluorescent supramolecular biosensor be interacting with the first peptide of another supramolecular building block when forming the fluorescent supramolecular biosensor.

The third peptide contains a fluorophore at one amino acid sequence selected from the 2nd-15th amino acid sequences, specifically the 2nd amino acid sequence. It is because, if the fluorophore is located at the 15th amino acid sequence of the third peptide, the fluorescent supramolecular biosensor may not be structurally stabilized when the supramolecular building blocks are assembled. The 2nd amino acid sequence may be a lysine residue or an alanine residue and the fluorophore may be bound to the side chain amine group (ε-amino group) of the lysine residue or the side chain methyl group of the alanine residue.

Specifically, the fluorophore may be bound to the lysine residue of the third peptide. Most specifically, it may be bound to the side chain amine group of the 2nd lysine residue located from the C-terminal, so that the α-helical secondary structure is stably fixed in the finally formed supramolecular building block and, through this, the fluorescent supramolecular biosensor forms a stable structure even at high temperatures.

The fluorophore may be one selected from a group consisting of DEABA (p-(N,N-diethylamino)benzoic acid), SNAFL, SNARF, SNAFL, Calcium Green, Amplex Red, Texas Red, BIODIPY, Oregon Green, Alexa Fluor, Cascade Blue, Dapoxyl, coumarin, rhodamine, N-methyl-4-hydrazino-7-nitrobenzofurazan, dansylethylenediamine, dansylcadaverine and dansylhydrazine, more specifically one selected from a group consisting of DEABA and Dapoxyl, although not being specially limited thereto.

Specifically, the supramolecular building block according to the present disclosure may be represented by [Chemical Formula 1], as shown in FIG. 10, where $R_1$ is DEABA (p-(N,N-diethylamino)benzoic acid) or Dapoxyl.

In Chemical Formula 1, the blue amino acid sequences represent the first peptide and the third peptide. They are divided into the first peptide and the third peptide with respect to the lysine residue at the center.

The red amino acid sequence represents the second peptide.

The black amino acid sequence represents the linker.

The supramolecular building block according to the present disclosure has an average molecular weight of 20-25 kDa. Due to the small molecular weight and size and strong intermolecular interaction, it is stable even when stored at high temperatures for several days and is self-assembled in short time. The fluorescent supramolecular biosensor prepared from the self-assembly can form a highly ordered complex structure having complex functionality.

A plurality of the supramolecular building blocks having the structure described above are assembled to form the fluorescent supramolecular biosensor. The fluorescent supramolecular biosensor has plurality of receptors (second peptide) capable of binding to a specific bacterium on the outer surface, and the third peptide, which contains the fluorophore exhibiting difference fluorescence intensities depending on the structural change of the fluorescent supramolecular biosensor, and the first peptide, which forms the basic framework, are located at the core.

In the fluorescent supramolecular biosensor system, the coiled coil structure of the first peptide is transferred to the second peptide as the first and second peptides are bound to form the constrained cyclic peptide. As a result, the second peptide also has a coiled coil structure. Through this process, the fBS forms a tetrameric coiled coil structure formed as the four supramolecular building blocks are assembled.

Figure 3:
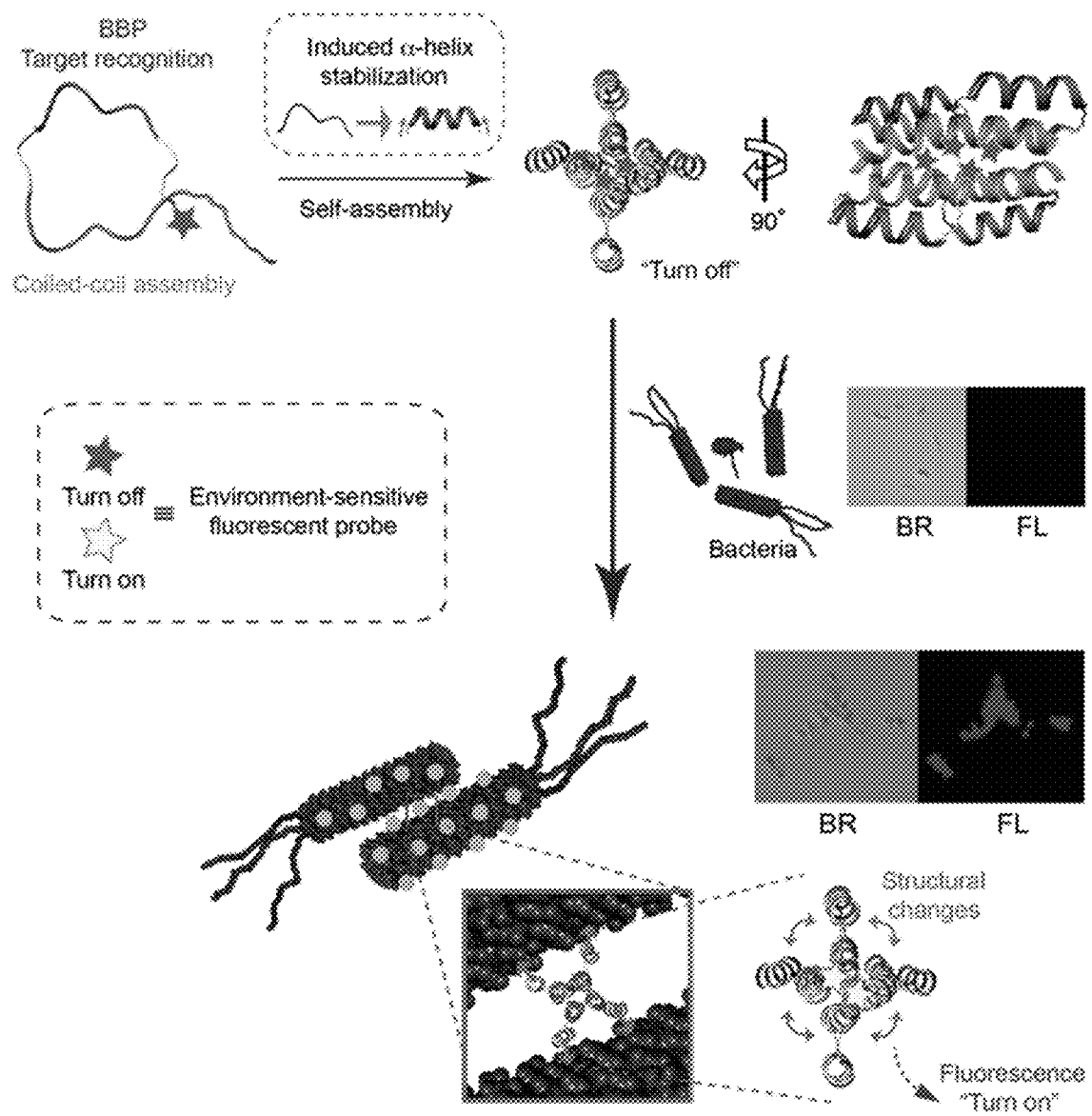
FIG. 3 shows the preparation process and operating principle of a fluorescent supramolecular biosensor according to the present disclosure. Specifically, eight supramolecular building blocks having a helical structure are bound to each other to form a fluorescent supramolecular biosensor which is a tetramer and the fluorescent supramolecular biosensor is 'turned on' by binding to a bacterium and emits fluorescence.

Referring to FIG. 3, when the fluorescent supramolecular biosensor is formed through the self-assembly of the supramolecular building blocks, a synthesized lariat-type peptide is self-assembled based on the coiled coil structure through interaction with another supramolecular building block.

First, the first peptide is converted, into a coiled coil (coil-to-helix) structure. This conversion is accompanied by the change in the coiled coil (coil-to-helix) structure of the second peptide (BBP). As a result, a lariat-type polypeptide (supramolecular building block) having a stabilized secondary structure is formed.

Consequentially, the fluorescent supramolecular biosensor is formed as a multimer as a plurality of the supramolecular building blocks are self-assembled when pH is 6.0-7.0 or ionic strength is 0.01-0.3 M. The number of the supramolecular building blocks is not particularly limited as long as the fluorescent supramolecular biosensor can be formed as a spherical nanoparticle with an average particle diameter of 5-20 nm. Most specifically, it may be a tetramer formed from the four supramolecular building blocks.

The tetrameric fluorescent supramolecular biosensor with a coiled coil structure is prepared as a spherical bilayer nanoparticle wherein the first peptide is located at the core and the helical structure-stabilized second peptide surrounds the core and, therefore, can exist for a long time very stably in aqueous state.

The α-helical structure of the second peptide is very important for recognition of the Gram-negative bacterium $E.$ $coli$. Despite the difference in size of the fluorescent supramolecular biosensor (5-10 nm) and the target bacterium $E.$ $coli$ (1-2 μm), the sensitivity, accuracy and selectivity of detecting the bacterium are superior because multiple binding sites are formed between them.

The degree of α-helical structure stabilization of the fluorescent supramolecular biosensor was measured by circular dichroism (CD) spectroscopy and the result was represented as a ratio of molar ellipticity at 220 nm and 208 nm ($[\theta]_{222}/[\theta]_{208}$). The fluorescent supramolecular biosensor maintains a molar ellipticity ($[\theta]_{222}/[\theta]_{208}$) of 1-0.8 at 20-90° C. This means that the fluorescent supramolecular biosensor stably maintains the coiled coil structure which plays an important role in binding to the bacterium even at the high temperature of 90° C. That is to say, the fluorescent supramolecular biosensor according to the present disclosure can maintain the ability of detecting the specific bacterium even at high temperatures because it is designed to have the structure described above.

That is to say, when the fluorescent supramolecular biosensor is not contacted with the specific bacterium, it is in the 'turn off' state exhibiting no fluorescence because no structural change occurs.

But, when the fluorescent supramolecular biosensor is bound to the target bacterium, the secondary stereostructure (coiled coil structure) of the supramolecular building block forming the fluorescent supramolecular biosensor is changed and fluorescence emission or color development from the fluorophore existing in each supramolecular building block is induced ('turn on').

The target bacterium can be detected based on this principle and the related process is illustrated specifically in FIG. 3.

Because the hydrophobic interaction between the first peptides existing in the supramolecular building blocks are used, the second peptide existing in the supramolecular building block is formed to be effectively exposed from the outer surface of the fluorescent supramolecular biosensor.

When the number of the supramolecular building blocks used to form the fluorescent supramolecular biosensor is four, a quadruple helix is formed through the hydrophobic interaction between the first peptides existing in the supramolecular building blocks and the angle between the supramolecular building blocks is 90°.

When the fluorescent supramolecular biosensor is contacted with the specific bacterium, a plurality of the second peptides existing on the outer surface of the fluorescent supramolecular biosensor bind specifically to a plurality of the specific bacteria and the presence of the specific bacterium can be detected based on the change in the fluorescence emission characteristics of the fluorophore bound to the third peptide as the structure of the fluorescent supramolecular biosensor is changed.

In addition, because the fluorescent supramolecular biosensor contains multiple receptors (second peptides) in one spherical nanoparticle, it is possible to detect a large number of the specific bacteria with a small quantity of the fluorescent supramolecular biosensor.

The bacterium detected by the fluorescent supramolecular biosensor of the present disclosure varies depending on the second peptide. When the second peptide of SEQ ID NO 3 or 4 is used, the fluorescent supramolecular biosensor may have specificity for E. coli. The fluorescent supramolecular biosensor for detecting E. coli exhibits 4-14 time superior selectivity for E. coli than other bacteria.

Another aspect of the present disclosure relates to a method for detecting a bacterium using the fluorescent supramolecular biosensor. The detection method may include a step of irradiating light for fluorescence excitation and a step of detecting fluorescence emission.

First, the fluorescent supramolecular biosensor is contacted with a sample from which a specific bacterium is to be detected. Specifically, the concentration of the fluorescent supramolecular biosensor may be 0.1 μM-1000 μM, although not being specially limited thereto.

Next, light for fluorescence excitation may be irradiated. The light irradiated to the fluorescent supramolecular biosensor for fluorescence excitation may have a wavelength of 300-500 nm. Also, the irradiated light may have a wavelength of 315-400 nm or 330-350 nm. Most specifically, it may have a wavelength of 338-341 nm. The light may be emitted from any light source for fluorescence excitation. Most specifically, the light source may be a laser light source.

Next, fluorescence emission may be detected. The emitted fluorescence may have a wavelength of 400-500 nm. Also, the wavelength may be 410-455 nm or 420-450 nm. Most specifically, the wavelength may be 431-446 nm.

Another aspect of the present disclosure relates to a method for preparing the fluorescent supramolecular biosensor, which includes:

I) a step of synthesizing a linear peptide containing: a first peptide; a second peptide bound to the first peptide; and a linker bound to the N-terminal of the second peptide from a resin;
wherein the N-terminal of the first peptide is a lysine residue, II) a step of preparing a cyclic peptide by cyclizing the linear peptide synthesized in the step I);

III) a step of preparing a supramolecular building block by binding a third peptide to a main chain amine group (α-amino group) of the lysine residue of the cyclic peptide; and IV) a step of inducing self-assembly by adding an aqueous solution to the supramolecular building block.

The present disclosure is directed to providing the supramolecular building block of a new structure by preparing the cyclic peptide by binding the second peptide to one site selected from the N-terminal of the linear peptide containing the first peptide having a coiled coil structure and the third peptide and the 4-6th turns with respect to the first turn in the coiled coil structure of the first peptide.

In order to prepare the supramolecular building block having the above-described structure, in the present disclosure, the linear peptide containing: the first peptide; the second peptide bound to the first peptide; and the linker bound to the N-terminal of the second peptide is prepared from the resin (step I).

The first peptide may have a lysine residue at the N-terminal. Accordingly, the second peptide may be bound to a side chain amine group (ε-amino group) of the lysine residue at the N-terminal of the first peptide.

Specifically, if the second peptide is bound to the side chain of the lysine residue at the N-terminal of the first peptide, the secondary stereostructure of the coiled coil structure of the first peptide may be fixed stably.

The first peptide is a peptide which forms a cyclic structure through grafting with the second peptide. Specifically, it contains an amino acid sequence located on a turn selected from the 4-6th turns with respect to the 1st turn of the first peptide.

The amino acid sequence located on one selected from the 4-6th turns is a lysine residue. Specifically, if it is not a lysine residue, it may be replaced with a lysine residue.

The first peptide may have a SEQ ID NO 1 or 2.

[SEQ ID NO 1]
Arg Leu Arg Lys Leu Arg Lys Lys Leu Arg Ser Gly
Ala

[SEQ ID NO 2]
Lys Glu Leu Glu Asp Lys Gln Glu Arg Leu Arg Lys
Leu Arg Lys Lys Leu Arg Ser Gly Ala

And, in the supramolecular building block, the second peptide is a peptide capable of specifically recognizing the target bacterium and forming interaction. It is not particularly limited as long as it contains an amino acid sequence capable of specifically binding to the specific bacterium and having a coiled coil structure (α-helix). Specifically, the amino acid sequence may be selected from SEQ ID NOS 3 or 4.

[SEQ ID NO 3]
Arg Leu Leu Phe Arg Lys Ile Arg Arg Leu Lys Arg
Lys

[SEQ ID NO 4]
Phe Lys Arg Ile Val Gln Arg Ile Lys Asp Phe Leu
Arg Lys

The first peptide and the second peptide may be connected directly or via a linker. The linker improves the flexibility and stability of the first peptide and the second peptide. The linker may be one or more selected from compounds represented by Chemical Formula 3 and Chemical Formula 4, an amino acid sequence wherein 1-5 glycine(s) is(are) bound continuously, one or more amino acid sequence selected from a group consisting of glycine-serine, glycine-serine-glycine-serine, glycine-glycine-serine and glycine-glycine-glycine-serine and a combination of one of the above compounds and one of the above amino acid sequences.

[Chemical Formula 3]

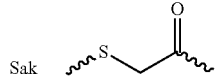

-continued

[Chemical Formula 4]

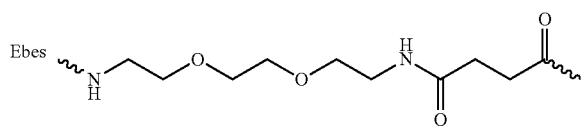

The third peptide not forming the cyclic peptide serves as a tail extended from, the cyclic structure of the lariat. The first and third peptides are synthesized first as linear peptides and they are divided into the first and third peptides as the second peptide is grafted. Specifically, the third peptide may contain an amino acid sequence which forms a 5-7th, 6-7th or 7th turn based on the 1st turn of the cyclic peptide.

Next, the cyclic peptide is prepared by cyclizing the linear peptide synthesized in the step I (step II).

The linear peptide may be prepared into the cyclic peptide by inducing cyclization through binding between the C-terminal of the linear peptide and the N-terminal of the linear peptide.

Specifically, the cyclization may be conducted by diisopropylethylamine (DI PEA).

Finally, the third peptide is bound to the main chain amine group (α-amino group) of the lysine residue of the cyclic peptide prepared in the step II.

A protecting group is removed first from the lysine residue in order to bind the second peptide to the main chain amine group of the lysine residue having the first and second peptides bound in the cyclic peptide and then the third peptide is synthesized from the main chain amine group of the lysine residue using the solid-phase peptide synthesis technique.

The third peptide not forming the cyclic peptide serves as a tail extended from, the cyclic structure of the lariat. The first and third peptides are synthesized first as linear peptides and they are divided into the first and third peptides as the second peptide is grafted. Specifically, the third peptide may contain an amino acid sequence which forms a 5-7th, 6-7th or 7th turn based on the 1st turn of the cyclic peptide.

The third peptide may contain SEQ ID NO 5 or 6.

[SEQ ID NO 5]
Gly Asn Ala Asp Glu Leu Tyr Lys Glu Leu Glu Asp

Lys Gln

[SEQ ID NO 6]
Gly Asn Ala Asp Glu Leu Tyr

Although the third peptide contains the α-helical amino acid sequence, it exists as an unfolded linear form because it protrudes out of the supramolecular building block rather than being located in the cyclic structure. But, when a multimer is formed in a solvent through self-assembly, it forms a coiled coil structure by interacting with the first peptide of another supramolecular building block.

The third peptide may contain a fluorophore at one amino acid sequence selected from the 2nd-15th amino acid sequences. Specifically, it may contain the fluorophore at the 2nd amino acid sequence for a stabilized structure of a lariat-type building block. The 2nd amino acid sequence may be a lysine residue or an alanine residue and the fluorophore may be bound to the side chain amine group (ε-amino group) of the lysine residue or the side chain methyl group of the alanine residue.

Specifically, the fluorophore may be bound to the lysine residue of the third peptide. Most specifically, it may be bound to the side chain amine group of the 2nd lysine residue located from the C-terminal, so that the coiled coil structure, i.e., the α-helical secondary structure, is stably fixed in the finally formed supramolecular building block and, through this, the structural stability is greatly improved in a buffer or an aqueous solution.

The fluorophore may be one selected from a group consisting of DEABA (p-(N,N-diethylamino)benzoic acid), SNAFL, SNARF, SNAFL, Calcium Green, Amplex Red, Texas Red, BIODIPY, Oregon Green, Alexa Fluor, Cascade Blue, Dapoxyl, coumarin, rhodamine, N-methyl-4-hydrazino-7-nitrobenzofurazan, dansylethylenediamine, dansylcadaverine and dansylhydrazine, more specifically one selected from a group consisting of DEABA and Dapoxyl, although not being specially limited thereto.

Specifically, the supramolecular building block according to the present disclosure may be represented by [Chemical Formula 1], as shown in FIG. 10, where $R_1$ is DEABA (p-(N,N-diethylamino)benzoic acid) or Dapoxyl.

In FIG. 10, the blue amino acid sequences represent the first peptide and the third peptide. They are divided into the first peptide and the third peptide with respect to the lysine residue at the center.

The red amino acid sequence represents the second peptide.

The black amino acid sequence represents the linker.

Then, in the step IV, the self-assembly of the supramolecular building block is induced by adding the aqueous solution.

Specifically, the aqueous solution may have a pH of 6.0-7.0 or an ionic strength of 0.01-0.3 M. Under this condition, the supramolecular building block is self-assembled to form a tetramer.

Hereinafter, the present disclosure will be described in more detail through examples. However, it should not be construed that the scope of the present disclosure is restricted or limited to the examples. Also, it is obvious that those of ordinary skill can easily carry out the present disclosure for the matters specific experimental results are not provided based on the disclosure of the present disclosure including the examples and that such changes and modifications are included in the scope of the appended claims.

In the following examples, only the representative experimental results of examples and comparative examples are presented.

Materials

Fmoc-amino acids and coupling reagents were purchased from Novabiochem (Germany) and Anaspec (USA). General chemicals were acquired from Sigma-Aldrich (USA) and Merck (Germany). Dapoxyl succinimidyl ester was purchased from Thermo Fisher Scientific (USA). Oligonucleotides were purchased from Integrated DNA Technologies. Yeast tRNA was purchased from Ambion.

Experimental Methods

1) Circular Dichroism Spectroscopy

CD spectra were recorded using the Chirascan circular dichroism spectrometer equipped with a Peltier temperature controller (Applied Photophysics Ltd.). The CD spectra of samples were recorded at 190-260 nm.

The concentration of pDE of Preparation Example 1 and pDA of Preparation Example 2 was 20 μM. The supramolecular building blocks of Preparation Examples 1 and 2 were dissolved in PBS (phosphate-buffered saline, 20 mM potassium phosphate, pH 7.0, 150 mM potassium fluoride).

2) Dynamic Light Scattering (DLS)

The particle size distribution of samples was investigated using Malvem Zetasizer Nano ZS90 (Malvern Instrument, UK) equipped with a He—Ne laser (max. 4 mW) operating at a wavelength of 633 nm. The temperature was set to 25° C.

3) Fluorescence Spectroscopy

The PerkinElmer LS-55 fluorescence spectrophotometer was used for fluorescence spectroscopy. Measurement was made at 340 nm in order to measure the fluorescence from Dapoxyl existing in a sample. A 5-nm reference pass band was used for the measurement together with excitation and emission slits. The concentration of a fluorescent supramolecular biosensor formed from the pDE of Preparation Example 1 and a fluorescent supramolecular biosensor formed from the pDA of Preparation Example 2 was 20 μM.

4) Small-Angle X-Ray Scattering (SAXS)

Small-angle X-ray scattering measurement was carried out using the 4C SAXS II beamline (BL) of the Pohang Accelerator Laboratory (PAL). A light source from the In-Vacuum Undulator 20 (IVU 20:1.4 m in length, 20 mm period) of the Pohang Light Source II storage ring was focused on a sample, utilizing a vertical focusing toroidal mirror coated with rhodium and monochromatized with a Si (111) double crystal monochrmator (DCM,) yielding an X-ray beam of a wavelength of 0.675 Å.

The solution sample cell with mica windows was 10 μm thick with a volume of 50 μL and it had an X-ray beam path of 0.8 mm. The sample was irradiated at room temperature for 30 seconds. The scattered radiation was measured using a 2-dimensional (2D) charge-coupled detector (Mar USA, Inc.) located at a distance of 1 m (0.04 Å$^{-1}$<q<0.50 Å$^{-1}$) from the sample. The SAXS data were collected in five successive frames of 0.1 minute each to minimize radiation loss. Each 2D SAXS pattern was averaged from the beam center and normalized to the transmitted X-ray beam intensity which was monitored with a scintillation counter placed behind the sample. The scattering of water was used as the experimental background. In order to acquire structural information from the SAXS data, the pair distance distribution function p(r) was obtained using the indirect Fourier transform [Equation 1] using the GNOM software.

$$p(r) = \frac{1}{2\pi^2 r} \int_0^\infty qrI(q)\sin(qr)dq \qquad \text{[Equation 1]}$$

where q is momentum transfer (q=(4π/λ) sin θ, wherein 2θ is the scattering angle and λ is the wavelength of the X-ray beam) and r is the distance between the paired scattering elements.

The maximum diameter ($D_{max}$) of a given macromolecule can be obtained from the distance at which p(r) approaches zero.

The radius of gyration ($R_{g,p(r)}$) is calculated from [Equation 2].

$$R_{g,p(r)}^2 = \frac{\int_A^\infty r^2 p(r)dr}{2\int_A^\infty p(r)dr} \qquad \text{[Equation 2]}$$

The ab-initio shape of the peptide measured, in water at low resolution was reconstructed using the DAMMIF software. Surface rendering in the structural models was achieved using Discovery Studio 1.6 (Accelrys, Inc.).

5) Sedimentation Velocity Analytical Ultracentrifugation

Analytical ultracentrifugation was conducted using the ProteomeLab XL-A analytical centrifuge (Beckman Coulter, Inc.), the An 60Ti rotor, the 2-sector Epon centerpiece and a quartz window at 50000 rpm. The optical path length of the cell was 12 mm. The recorded data were analyzed with the SEDFIT program.

6) Bacterial Detection Experiment

*Escherichia coli* (*E. coli*, DH5a) and other bacteria (*Staphylococcus aureus*, *Pseudomonas aeruginosa*, *Bacillus cereus*, *Bacillus atrophaeus* and *Bacillus thuringiensis*) were purchased from Invitrogen (USA) and the Korean Collection for Type Cultures (KCTC, Korea).

The concentration of the bacterium was determined by smearing the serially diluted bacterium solution onto an agar plate. Specifically, after culturing the bacterium smeared onto the agar plate overnight, the colony-forming unit (CFU) was calculated by counting the number of colonies formed.

For bacterium sensing, 16 μL of a biosensor SPN (40 NM) was mixed with 384 μL of the bacterium solution and fluorescence was measured. The fluorescence spectrum was measured using the PerkinElmer LS-55 fluorescence spectrophotometer. A quartz cuvette with a path length of 1 cm was used. For the measurement of fluorescence from DEABA and Dapoxyl, the sample was exited at 280 nm and 340 nm, respectively, and measurement was made using 5-nm emission and excitation slits.

Preparation Examples 1 and 2. Synthesis of Supramolecular Building Blocks (pDE and pDA)

Supramolecular building blocks represented by Chemical Formula 1 were prepared. The one with $R_1$ being DEABA is a supramolecular building block of Preparation Example 1 (hereinafter, also referred to as pDE) and the one with R, being Dapoxyl is a supramolecular building block of Preparation Example 2 (hereinafter, also referred to as pDA).

Peptides were synthesized from the Rink Amide MBHA resin LL (Novabiochem) using the Tribute peptide synthesizer (Protein Technologies, Inc.) according to the standard Fmoc protocol. For Cys and Lys, methoxytrityl (Mmt) and N-[1-(4,4-dimethyl-2,6-dioxocyclohex-1-ylidene)ethyl] (Dde) were used as standard amino acid protecting groups, respectively.

For side chain-terminal cyclization, bromoacetic acid was coupled first to the N-terminal of the resin-bound peptide. Before adding to the resin, a first mixture of bromoacetic acid (28 mg, 200 μmol) and diisopropylcarbodiimide (15.5 μL, 100 μmol) was incubated for 10 minutes in NMP for activation of carboxyl groups.

After adding the first mixture to the resin, reaction was conducted for 1 hour at room temperature with shaking. For orthogonal deprotection of Mmt from the cysteine residue, the resin was treated with a DCM (1% trifluoroacetic acid (TFA)) solvent for a predetermined time (from 1 minute up to 10 minutes) after the reaction was completed.

Intramolecular cyclization was conducted in 3 mL of a NMP solution (1% diisopropylethylamine (DIPEA)) while shaking overnight at room temperature.

The deprotection of Dde from Lys(Dde) was conducted using a DMF (2% hydrazine) solvent.

A segment (third peptide) which serves as a tail in a lariat-type supramolecular building block was bound using the standard Fmoc protocol. For fluorescence labeling of Dapoxyl, the leucine reside of the segment serving as the tail was replaced with Lys(Dde) and Dapoxyl® succinimidyl ester was conjugated to the orthogonal position of the deprotected lysine residue. Finally, for deprotection and separation from the resin, the resin-bound peptide was treated with a cleavage cocktail [trifluoroacetic acid (TFA)/triisopropylsilane (TIS)/water] (95:2.5:2.5) for 3 hours and then triturated with tert-butyl methyl ether. The peptide obtained through this process was purified by reversed-phase HPLC (water/acetonitrile with 0.1% TFA). The molecular weight of the peptide was measured by MALDI-TOF (matrix-assisted laser desorption/ionization time-of-flight) mass spectrometry (Microflex LRF20, Bruker). α-Cyano-4-hydrocinnamic acid (CHCA) was used as a substrate. The concentration of the peptide was measured in water/acetonitrile (1:1) using the molar extinction coefficient of Dapoxyl (21526 $M^{-1}$ $cm^{-1}$) at 340 nm using a spectrophotometer.

Figure 2A:
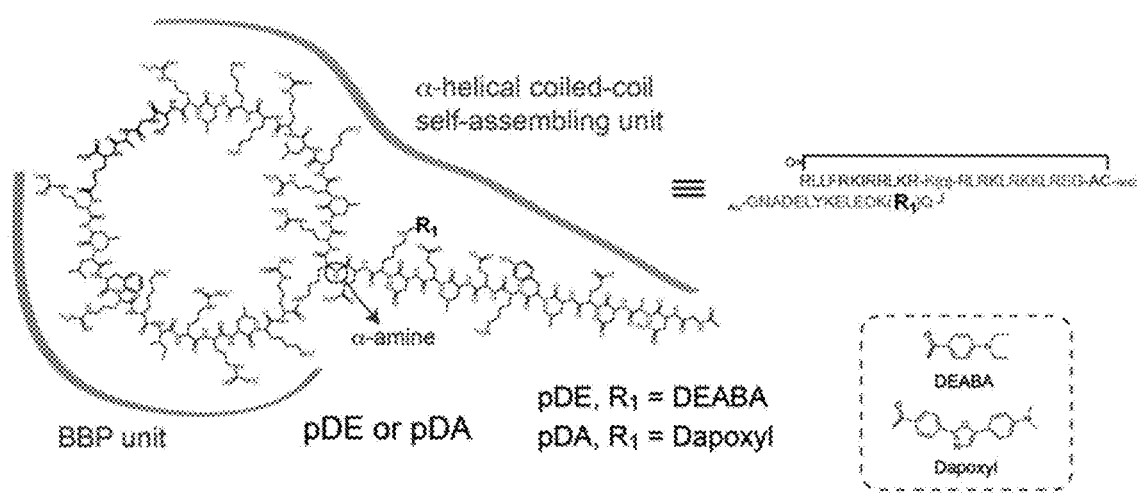
FIGS. 2A and 2B show the structures of various supramolecular building blocks according to the present disclosure. A fluorescent supramolecular biosensor according to the present disclosure is a tetramer formed from the four supramolecular building blocks. The supramolecular building block is a lariat-type peptide composed of a first peptide having a coiled coil structure, a second peptide (BBP) capable of recognizing a target bacterium and a third peptide having a fluorophore bound.

The prepared supramolecular building block is composed of a first peptide of SEQ ID NO 1, a second peptide of SEQ ID NO 3 and a third peptide of SEQ ID NO 5 and may be represented by Chemical Formula 1 (see FIG. 2A).

Preparation Example 3. Synthesis of Supramolecular Building Block (pDEε)

A supramolecular building block ($R_2$=DEABA) represented by Chemical Formula 2, shown in FIG. 11, was prepared in the same manner as in Preparation Example 1.

Figure 2B:
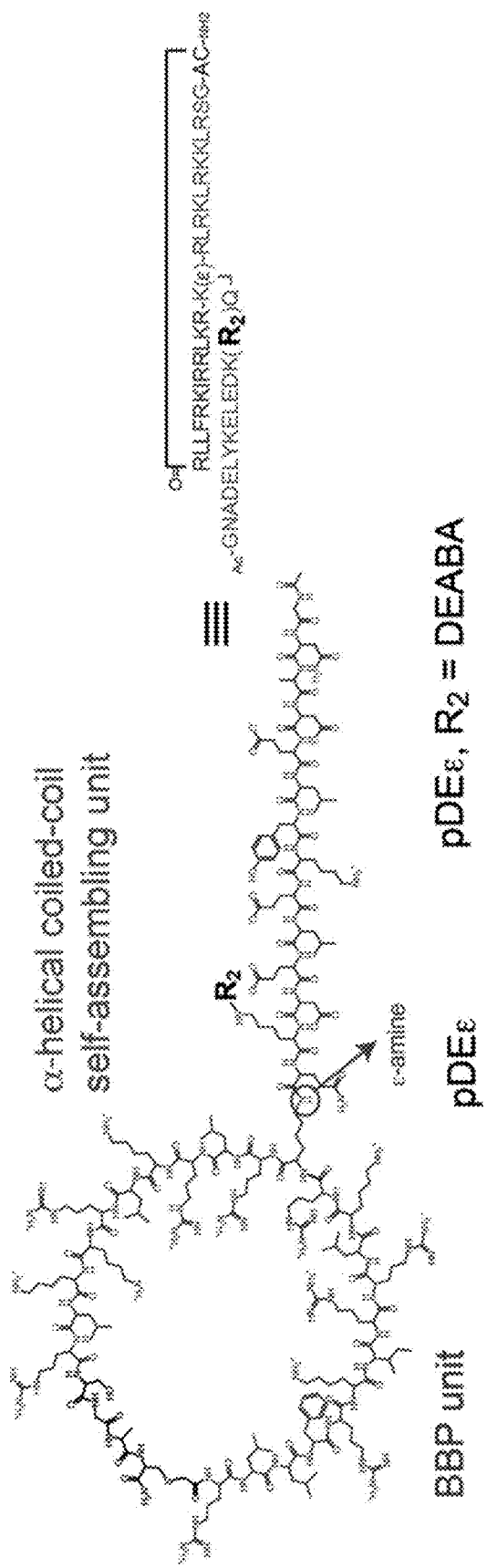

Specifically, the supramolecular building block of Preparation Example 3 has the same peptide sequence as that of Preparation Example 1 but is different in that the first peptide and the second peptide are bound centered around the lysine residue, the second peptide being bound to the main chain amine group of the lysine residue and the third peptide being bound to the side chain amine group of the lysine residue (see FIG. 2B).

Test Example 1. Self-Assembly Characteristics of pDE Prepared in Preparation Example 1

FIGS. 5A to 5C show results of investigating whether the supramolecular building block (pDE) prepared in Preparation Example 1 forms a tetramer and operates as a fluorescent supramolecular biosensor when dissolved in a solvent. FIG. 5A shows the CD spectra obtained when the pDE of Preparation Example 1 was dissolved in pure water (red) and PBS (20 mM potassium phosphate, 150 mM NaCl, pH 7.0; blue), respectively, and FIG. 5B shows fluorescence intensity depending on wavelength.

FIG. 5C shows the SAXS result for the stereostructure of the fluorescent supramolecular biosensor formed as a tetramer from the pDE prepared in Preparation Example 1. The upper graph shows the SAXS spectrum of the fluorescent supramolecular biosensor formed from the pDE of Preparation Example 1 as a tetramer and the lower graph shows the distance distribution function p(r) for the fluorescent supramolecular biosensor formed from the pDE of Preparation Example 1 based on the analysis of the experimental SAXS data. The p(r) function was obtained using the GNOM software. Representative structural models used for simulation of the SAXS data are shown at the right side of the graphs ([pDE]=20 μM).

As seen from FIGS. 5A to 5C, the pDE of Preparation Example 1 was fluorescence-labeled with DEABA (p-(N,N-diethylamino)benzoic acid). The DEABA was bound to the side chain amine (ε-amine) group of the lysine reside replacing the leucine reside of the third peptide which forms the hydrophobic core of the fluorescent supramolecular biosensor formed as the tetramer: The DEABA exhibits twisted intramolecular charge transfer (TICT), which affects the fluorophore through solvent polarity, viscosity and restricted molecular motion.

Referring to FIG. 5A, the CD spectrum of the pDE of Preparation Example 1 reveals that it has a random coil structure in pure water. In contrast, when the pDE of Preparation Example 1 was dissolved in PBS, negative bands were observed at 208 nm and 222 nm, which suggest the α-helical structure.

Through this, it can be seen that the supramolecular building block according to the present disclosure is effectively self-assembled to form the fluorescent supramolecular biosensor under a high ionic strength condition because hydrophobic interaction is increased and protonated state can be maintained at neutral pH.

As seen from FIG. 5B, when the pDE of Preparation Example 1 was dissolved in PBS, the band at 450 nm (emission from BEABA in the $^1$La-type) was strongly increased. That is to say, it was confirmed from the fluorescence measurement that the pDE of Preparation Example 1 can be self-assembled to form a fluorescent supramolecular biosensor in a solvent-dependent manner.

When the CD spectra of the pDE of Preparation Example 1 and the pDEεS of Preparation Example 3 with slight modification in the backbone structure were measured (not shown), neither α-helix stabilization nor fluorescence emission at 450 nm was observed. Through this, it was confirmed that the pDEεS of Preparation Example 3 with slight modification in the backbone structure is not self-assembled effectively.

From the CD spectra and fluorescence intensity vs. wavelength graphs, it was confirmed that the supramolecular building block according to the present disclosure is self-assembled in PBS (high ionic strength and neutral pH) to form the fluorescent supramolecular biosensor.

The fluorescent supramolecular biosensor formed from the pDE of Preparation Example 1 was simulated based on the small-angle X-ray scattering (SAXS) analysis result in PBS as shown in FIG. 5C. The radius of gyration ($R_{g.p(r)}$: 23.2 Å), maximum diameter ($D_{max}$: 63 Å) and SAXS envelope fit were determined.

The tetramer formed from the four pDE of Preparation Example 1 or pDA of Preparation Example 2 was self-assembled into a bilayer form. It was confirmed through sedimentation velocity analytical ultracentrifugation (AUC) measurement and the result is shown in Table 1. Table 1 shows the AUC result for the tetrameric nanostructure formed from the four pDE of Preparation Example 1 or pDA of Preparation Example 2.

TABLE 1

| Supramolecular building block | Calc'd $M_r$ for tetramer | Measured $M_r$ |
|---|---|---|
| Preparation Example 1 pDE | 21.4 kDa | 20.2 kDa |
| Preparation Example 2 pDA | 21.9 kDa | 22.4 kDa |

Test Example 2. Bacterium Detection Ability of Fluorescent Supramolecular Biosensors Formed from pDE and pDA FIGS. 6A to 6C show results of investigating the change in fluorescence after adding the pDE of Preparation Example 1 to mixture solutions of *E. coli* and *Staphylococcus aureus* (*S. aureus*) at various concentrations: in FIG. 6A $10^5$ CFU/mL, in FIG. 6B, $10^6$ CFU/mL, and in FIG. 6C, $10^5$ CFU/mL. All experiments were conducted at room temperature. In the graphs, the red lines are the fluorescence signals of Preparation Example 1 pDE mixed with *E. coli* and the blue lines are the fluorescence signals of Preparation Example 1 pDE mixed with *Staphylococcus aureus*.

As seen from FIGS. 6A to 6C, the pDE of Preparation Example 1 showed significantly improved ability of detecting the specific bacterium as compared to the existing method.

A fluorescent supramolecular biosensor was prepared by dissolving the pDE of Preparation Example 1 in PBS. After adding bacteria of various concentrations and mixing through gentle pipetting, fluorescence intensity was measured. As the concentration of the target bacterium *E. coli* was increased, the band intensity of the fluorescent supramolecular biosensor was decreased. In contrast, when it was mixed with the nonspecific bacterium *Staphylococcus aureus*, the band intensity was maintained constant.

Through this, it was confirmed that, when the fluorescent supramolecular biosensor prepared from the supramolecular building block pDE of the present disclosure is mixed with the target bacterium, multiple interactions are formed with the bacterium and this binding leads to distortion of the 3-dimensional structure of the pDE (supramolecular building block) and decreased fluorescence intensity of the pDE of Preparation Example 1.

This suggests that a supramolecular building block can be developed by binding a peptide which forms binding sensitively to the environment through reversible self-assembly.

Test Example 3. Characterization of Fluorescent Supramolecular Biosensor Prepared from pDA of Preparation Example 2

Because Dapoxyl shows significant polarity-dependent change in intensity as well as Stokes shift as compared to DEABA, the characteristics of the fluorescent supramolecular biosensor formed from the pDA of Preparation Example 2, wherein the DEABA fluorophore of the pDE of Preparation Example 1 was replaced with Dapoxyl, were analyzed.

From CD, SAXS and AUC analyses, it was confirmed that the pDA of Preparation Example 2 was self-assembled into a fluorescent supramolecular biosensor having an α-helical coiled coil structure similarly to the pDE of Preparation Example 1. Through this, it can be seen that the fluorophore bound to the third peptide does not interfere with the self-assembly behavior of the peptide.

FIGS. 7A to 7F shows a result of investigating the *E. coli* sensing and self-assembly of the fluorescent supramolecular biosensor prepared from pDA (Preparation Example 2). FIG. 7A shows the CD spectra of the fluorescent supramolecular biosensor prepared from pDA (Preparation Example 2) under various pH conditions and FIG. 7B shows the CD spectra of the pDA of Preparation Example 2 under various pH conditions. The pH was controlled with HCl or NaOH in the presence of 150 mM NaCl. [pDA]=20 µM.

FIG. 7C shows the normalized fluorescence emission spectra obtained by mixing *E. coli* of various concentrations with the fluorescent supramolecular biosensor prepared from the pDA of Preparation Example 2 and measuring fluorescence intensity and FIG. 7D shows the normalized fluorescence emission spectra obtained by mixing *Staphylococcus aureus* (*S. aureus*) of various concentrations with the fluorescent supramolecular biosensor prepared from the pDA of Preparation Example 2 and measuring fluorescence intensity.

FIG. 7E shows a graph obtained by measuring the change in fluorescence intensity (ΔI) depending on the bacterial concentration from the results of FIG. 7C and d). ΔI=fluorescence intensity of the mixture—fluorescence intensity when only the fluorescent supramolecular biosensor exists only.

FIG. 7F shows the selectivity of the fluorescent supramolecular biosensor according to the present disclosure when the concentration of each bacterium was $10^7$ CFU/mL. All the experiments in FIGS. 7A to 7F were conducted at room temperature.

As seen from FIG. 7A, the fluorescent supramolecular biosensor prepared from the pDA (Preparation Example 2) shows structural change depending on pH. It is thought that this is caused by the protonation of the amino acid residue of the first peptide in the coiled coil structure.

As seen from FIG. 7B, significant change in fluorescence wavelength was observed depending on pH change. As the solution pH is changed from acidic to basic, a Stokes shift of 150 nm was observed. At the intermediate state of pH 5, two peaks were identified. It is because, as the Dapoxyl fluorophore is added into the self-assembling peptide pDA of Preparation Example 2 having the coiled coil structure, it moves from the hydrophobic inside of the coiled coil structure outwards through self-assembly depending on pH change.

As seen from FIGS. 7C and 7D, in order to evaluate the ability of detecting bacteria, the fluorescent supramolecular biosensor formed from the pDA was mixed with bacteria at various concentrations and fluorescence was measured. As a result, the fluorescent supramolecular biosensor formed from the pDA of Preparation Example 2 showed no change at all when *Staphylococcus aureus* was added but spectral change was observed when it was mixed with *E. coli*.

As seen from FIG. 7E, it was confirmed that the fluorescent supramolecular biosensor formed from the pDA of Preparation Example 2 can detect *E. coli* at a concentration of $10^5$ CFU/mL discriminatingly from other bacteria.

As seen from FIG. 7F, it was confirmed that the fluorescent supramolecular biosensors formed from the pDE and the pDA according to the present disclosure exhibited much higher selectivity (about 4-14 times) for *E. coli* as compared to other bacteria.

Test Example 4. Reaction of Fluorescent Supramolecular Biosensor with Specific Bacterium FIG. 8A shows an optical microscopic image (BR: bright field) and a fluorescence image (FL) obtained by confocal laser scanning microscopy (CLSM) of a solution in which only *E. coli* exists and FIG. 8B shows an optical microscopic image (BR: bright field) and a fluorescence image (FL) obtained by confocal laser scanning microscopy (CLSM) of a mixture of the fluorescent supramolecular biosensor formed from the pDA of Preparation Example 2 and a bacterium (*E. coli*).

As seen from FIG. 8A, when only the *E. coli* existed, no fluorescence was observed and the bacterium was dispersed well as single cells.

In contrast, as seen from FIG. 8B, the fluorescent supramolecular biosensor according to the present disclosure was assembled when *E. coli* was added and blue fluorescence was observed. The aggregation of *E. coli* is due to the crosslinking between the bacteria formed by the fluorescent supramolecular biosensor according to the present disclosure.

Test Example 5. Thermal Stability of Fluorescent Supramolecular Biosensor

FIGS. 9A and 9B show results of investigating the thermal stability of the fluorescent supramolecular biosensor according to the present disclosure. FIG. 9A shows the CD spectrum ($[\theta]_{222}/[\theta]_{208}$) of the fluorescent supramolecular biosensor formed from the pDA of Preparation Example 2 depending on temperature change. FIG. 9B shows a result of calculating the change in fluorescence intensity ($\Delta I$) at 50° C. depending on the bacterial concentration. $\Delta I$=fluorescence intensity of the mixture—fluorescence intensity when only the fluorescent supramolecular biosensor exists only.

A globular protein composed of the supramolecular building block according to the present disclosure is very stable with $\Delta G_{folding}$ of about −5 to −10 kcal/mol. A protein with low stability tends to be denatured and aggregate easily. Because general biosensors employ natural proteins susceptible to thermal denaturation as receptors, they are difficult to be stored for a long time, are restricted in applications and have low selectivity for target substances.

As seen from FIG. 9A, the fluorescent supramolecular biosensor formed from the pDA of Preparation Example 2 stably maintained the coiled coil structure regardless of temperature (20-90° C.). That is to say, the fluorescent supramolecular biosensor maintained $[\theta]_{222}/[\theta]_{205}$, which is indicative of the stability of the coiled coil structure, at 1-0.8. Accordingly, it can be seen that the fluorescent supramolecular biosensor according to the present disclosure can ensure structural stability with high efficiency even at high temperatures.

As seen from FIG. 9B, the fluorescent supramolecular biosensor according to the present disclosure (pDA SPN) showed remarkably superior selectivity for *E. coli* even at the high temperature of 50° C.

In conclusion, it was confirmed that the fluorescent supramolecular biosensor according to the present disclosure, which is formed as the four supramolecular building blocks are assembled, can recognize multiple bacteria and can stably maintain the coiled coil structure even at high temperatures.

What is claimed is:

1. A fluorescent supramolecular biosensor for detecting a bacterium, comprising a plurality of supramolecular building blocks composed of:
   (1) a first peptide having a coiled coil structure;
   (2) an α-helical second peptide binding specifically to a specific bacterium; and
   (3) a third peptide having a fluorophore bound, wherein the supramolecular building block is a lariat-type polypeptide wherein the first and second peptides are bound centered around a lysine residue to form a linear peptide, the linear peptide forms a cyclic structure as both ends of are bound through a cyclization process and the third peptide is bound to a nitrogen atom of a main chain amine group (α-amine group) of the lysine residue of the linear peptide.

2. The fluorescent supramolecular biosensor according to claim 1, wherein the fluorescent supramolecular biosensor is a tetramer formed from the four supramolecular building blocks.

3. The fluorescent supramolecular biosensor according to claim 1, wherein the supramolecular building block further comprises a linker connecting the first and second peptides.

4. The fluorescent supramolecular biosensor according to claim 1, wherein the first peptide is represented by SEQ ID NO 1 or 2.

5. The fluorescent supramolecular biosensor according to claim 1, wherein the second peptide is represented by SEQ ID NO 3 or 4.

6. The fluorescent supramolecular biosensor according to claim 1, wherein the third peptide is represented by SEQ ID NO 5 or 6.

7. The fluorescent supramolecular biosensor according to claim 1, wherein the supramolecular building block forms a tetramer through self-assembly when pH is 6.0-7.0 or ionic strength is 0.01-0.3 M.

8. The fluorescent supramolecular biosensor according to claim 1, wherein the fluorescent supramolecular biosensor shows change in the fluorescence signal of the fluorophore as a folded structure formed in the supramolecular building block is changed through binding to a target bacterium.

9. The fluorescent supramolecular biosensor according to claim 1, wherein the fluorescent supramolecular biosensor is a spherical nanoparticle with an average particle diameter of 5-20 nm.

10. The fluorescent supramolecular biosensor according to claim 1, wherein the supramolecular building block is represented by Chemical Formula 1:

[Chemical Formula 1]
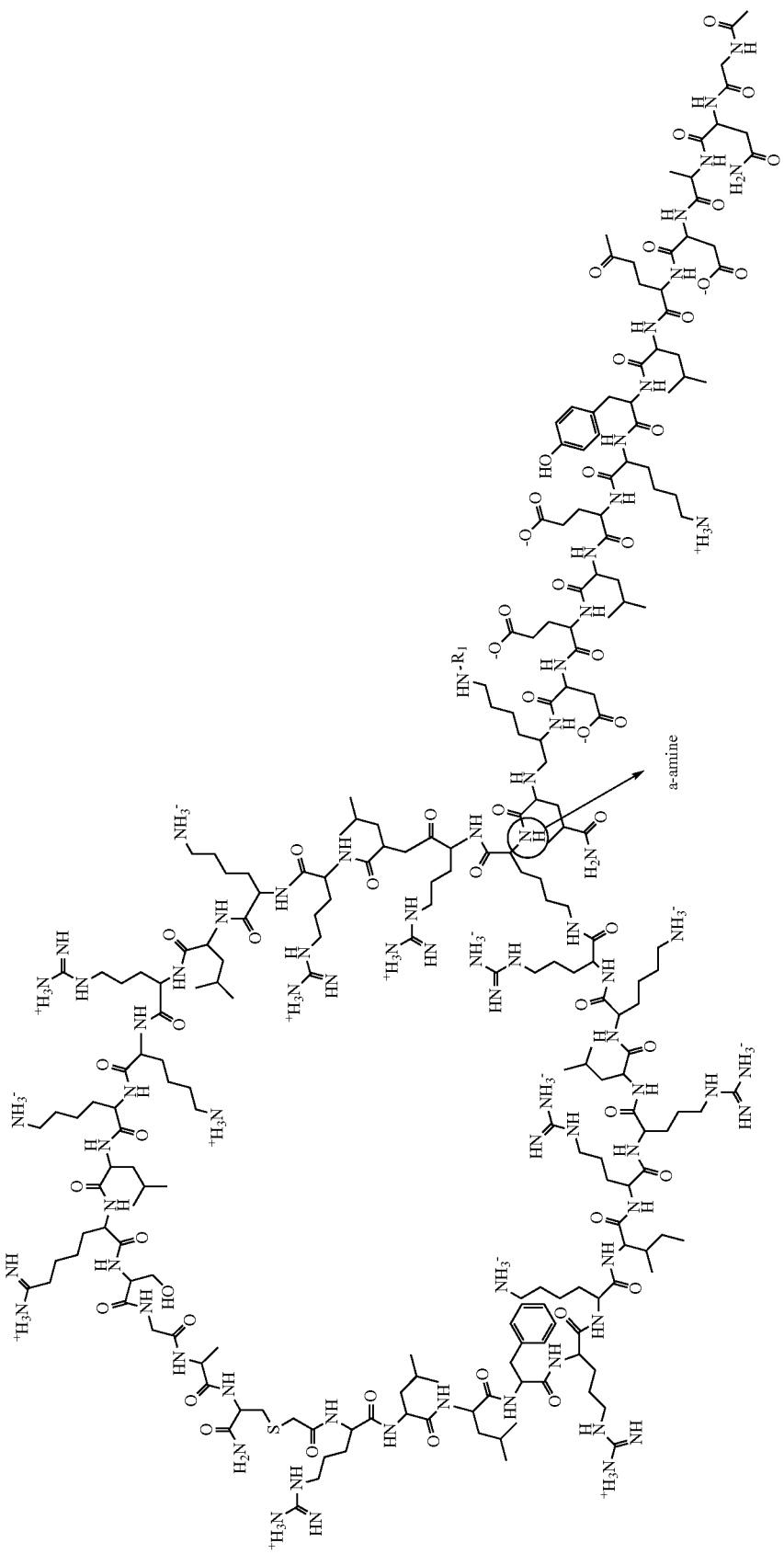

wherein $R_1$ is DEABA (p-(N,N-diethylamino)benzoic acid) or Dapoxyl.

11. The fluorescent supramolecular biosensor according to claim 1, wherein the fluorescent supramolecular biosensor maintains a molar ellipticity ($[\theta]_{222}/[\theta]_{208}$) of 1-0.8 at 20-90° C.

12. The fluorescent supramolecular biosensor according to claim 1, wherein the fluorophore is one selected from a group consisting of DEABA (p-(N,N-diethylamino)benzoic acid), SNAFL, SNARF, SNAFL, Calcium Green, Amplex Red, Texas Red, BIODIPY, Oregon Green, Alexa Fluor, Cascade Blue, Dapoxyl, coumarin, rhodamine, N-methyl-4-hydrazino-7-nitrobenzofurazan, dansylethylenediamine, dansylcadaverine and dansylhydrazine.

13. A method for detecting a bacterium using the fluorescent supramolecular biosensor according to claim 1, comprising:
  irradiating light for fluorescence excitation; and
  detecting fluorescence emission.

* * * * *